US009103766B2

(12) United States Patent
Schentag et al.

(10) Patent No.: US 9,103,766 B2
(45) Date of Patent: Aug. 11, 2015

(54) DEVICE AND METHOD FOR MONITORING AND QUANTIFYING ANALYTES

(71) Applicant: The Research Foundation of State University of New York, Amherst, NY (US)

(72) Inventors: Jerome J. Schentag, Amherst, NY (US); David T. D'Andrea, Amherst, NY (US); Frank V. Bright, Williamsville, NY (US)

(73) Assignee: Breath Diagnostics, LLC, Santa Clara, CA (US)

( * ) Notice: Subject to any disclaimer, the term of this patent is extended or adjusted under 35 U.S.C. 154(b) by 0 days.

(21) Appl. No.: 13/655,392

(22) Filed: Oct. 18, 2012

(65) Prior Publication Data

US 2013/0102018 A1    Apr. 25, 2013

Related U.S. Application Data

(60) Provisional application No. 61/548,390, filed on Oct. 18, 2011.

(51) Int. Cl.
| | |
|---|---|
| G01N 21/17 | (2006.01) |
| G01N 33/497 | (2006.01) |
| G01N 21/64 | (2006.01) |
| A61B 5/145 | (2006.01) |
| A61B 5/1455 | (2006.01) |
| A61B 5/00 | (2006.01) |

(52) U.S. Cl.
CPC .............. *G01N 21/17* (2013.01); *A61B 5/1455* (2013.01); *A61B 5/14507* (2013.01); *A61B 5/14532* (2013.01); *G01N 21/645* (2013.01); *G01N 21/6428* (2013.01); *G01N 33/497* (2013.01); *A61B 5/00* (2013.01); *G01N 2033/4975* (2013.01)

(58) Field of Classification Search
USPC ......................................... 422/68.1, 500, 404
See application file for complete search history.

(56) References Cited

U.S. PATENT DOCUMENTS 6,537,501 B1 *    3/2003    Holl et al. ..................... 422/537

* cited by examiner

*Primary Examiner* — Sam P Siefke
(74) *Attorney, Agent, or Firm* — Peters Verny, LLP

(57) ABSTRACT

The present invention can be described as an apparatus and cartridge for detecting the presence of an analyte in a fluid. The invention can also be described as a method of detecting the presence of an analyte in a fluid using the apparatus and cartridge. The method comprises the steps of clamping a sensor cartridge into a cartridge receiver of the apparatus, providing fluid to a fluid flow-path of the cartridge, illuminating at least a portion of a sensor, and using a photodetector to detect a change in the optical property of the sensor, wherein the change is caused by the presence or absence of an analyte in the fluid.

11 Claims, 21 Drawing Sheets

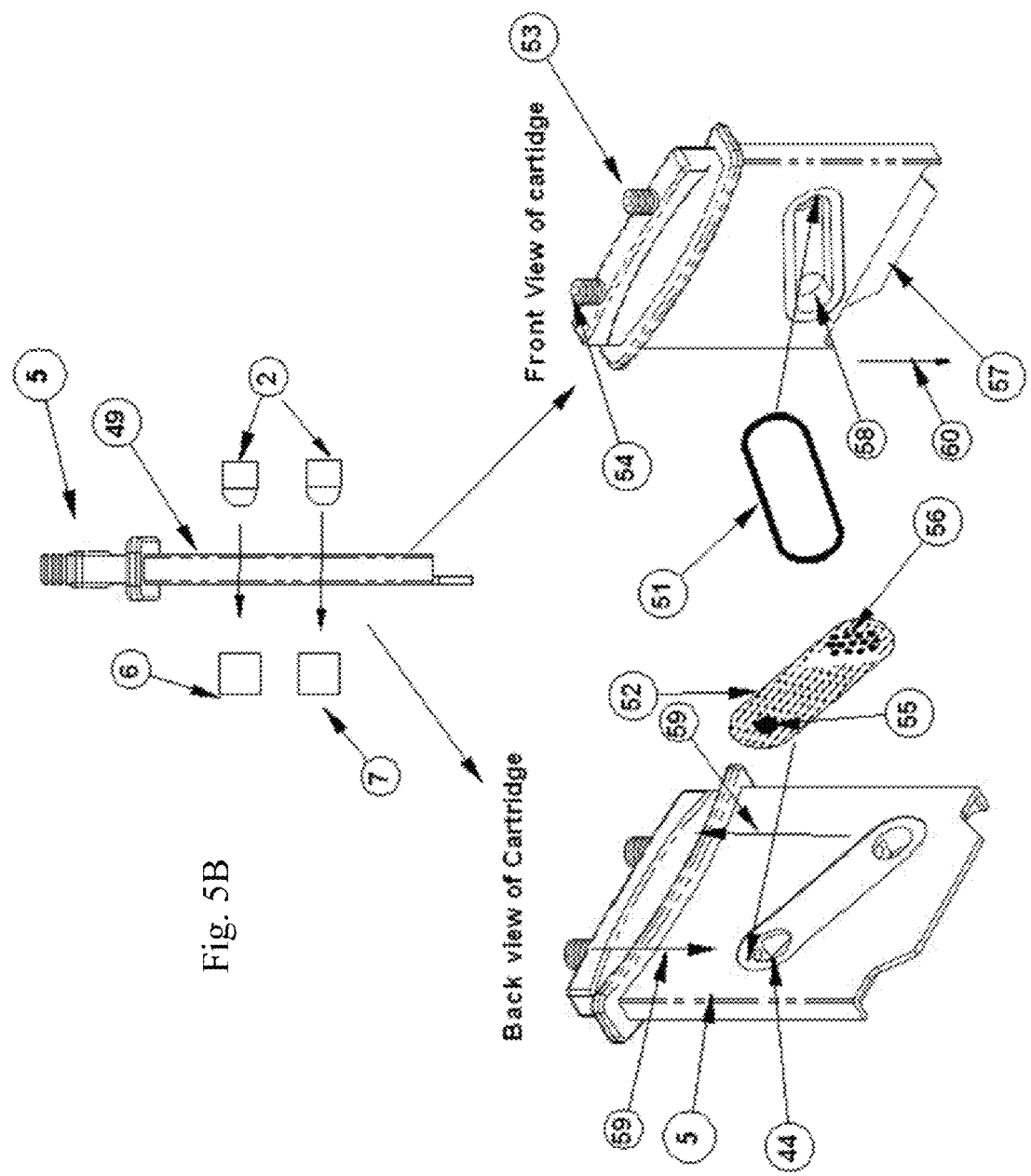

DEVICE AND METHOD FOR MONITORING AND QUANTIFYING ANALYTES

CROSS-REFERENCE TO RELATED APPLICATION

This application claims the benefit of priority to U.S. provisional patent application Ser. No. 61/548,390, filed on Oct. 18, 2011, the disclosure of which is hereby incorporated by reference.

FIELD OF THE INVENTION

This invention relates generally to the field of monitoring and quantification of analytes in a sample, and more particularly to a device and method for monitoring, quantifying, and/or measuring of analytes in breath, breath derived fluids, and any other suitable body fluid.

BACKGROUND OF THE INVENTION

Diabetes mellitus, a disease in which the pancreas fails to produce insulin or cells fail to respond to insulin for cellular metabolism of glucose, is a world-wide public health problem in terms of loss of quality of life and corresponding cost of care. Diabetes of the type-2 variety is a component of the so-called metabolic syndrome, which is a constellation of conditions linked to diabetes including obesity, hyperlipidemia, hypertension, immune system dysregulation, insulin resistance, hyperglycemia, atherosclerosis, and a series of cardiovascular events linked to these conditions. Metabolic syndrome complications are the primary causes of cardiovascular mortality in patients with diabetes and associated underlying conditions.

Data from the Diabetes Control and Complications Trial (DCCT), reported in 1993, show that quality of life may significantly be improved for people with diabetes if good control of blood sugar (glucose) levels is maintained. The primary benefit shown in DCCT was reduced complications from diabetes in cardiovascular disease progression.

To meet the current clinical recommendations of testing glucose, the most widely used, reliable and accurate method is a direct assay for glucose in a small amount of, typically, venous blood. Patients with certain kinds of diabetes must perform these tests on multiple occasions in each day. Handheld instruments, which measure the amount of glucose based on the interaction of glucose with reagents pre-deposited on test strips, are now widely available. Typically these instruments detect the amount of glucose in blood to plus or minus 20%, based on specific enzymatic reactions using microliter samples of blood.

To reduce pain and inconvenience of existing blood glucose monitoring devices, alternatives to blood glucose assays have been attempted. Breath testing for glucose has been implemented by condensation of exhaled breath with assay of the resulting condensate for glucose using sensitive laboratory instruments such as Mass Spectrometry. For a variety of reasons chiefly resulting from technical difficulties with the accurate measurement of the amount of breath actually involved in the production of condensate, there is no acceptable and available handheld, consumer friendly device to measure glucose concentrations in breath. Furthermore, current attempts at breath monitoring are not applied to other analytes. First, the concentrations of glucose in condensate of breath are below the sensitivity of the methods used in handheld meters for blood, such as electrochemistry and electroimpedance. So, it is not possible to sample breath with these single use test strip devices and read accurate breath glucose concentrations. Even if it became technically possible to measure glucose of 0.4 mmol in breath with a test strip, the measurement of condensed breath is subject to a great number of inaccuracies of breathing rate, temperature, electrolyte content and other aspects of breath itself that prevent this method from being applied successfully on a handheld device used by consumers. Another challenge of breath condensate is the difficulty with reproducibly collecting each breath in an identical manner, and the varied amounts of free water that is found in breath samples of different patients. Those skilled in the art of exhaled breath condensate measurement correct the collected breath sample by measuring its chloride concentration and use the chloride concentration to correct the measured glucose concentration for the amount of breath actually collected and the amount of water in the breath. This method suffers from the additional challenges of assay of chloride in a timely manner and from the inaccuracy that occurs in both measurements from factors not controlled by adjusting the results for breath chloride concentration.

While the chemistry for these tests is considered reliable, and the manufacturers of the test strips have demonstrated good quality control within the FDA standard of +/−20%, current self-testing for glucose remains a conscious process in which the diabetic must elect to take a blood sample and do the assay protocol for the hand-held instrument of choice. The primary failure for diabetics to do frequent self-testing for blood glucose levels, as recommend by the conclusions of the DCCT, is the pain associated with obtaining blood samples on a frequent schedule as well as the inconvenience of this blood testing process, particularly in public places.

Another issue is the need for more sensitive assays for glucose. Unfortunately, sensitive methods such as enzyme-linked immunosorbent assays (ELISA) are not useful for glucose measurement because glucose is not immunogenic and therefore not amenable to immune antibody assays such as ELISA. So in order to measure glucose at concentrations of 0.4 mmol such as found in breath, it is heretofore been necessary to collect condensate from a large amount of breath in a precise laboratory environment and to employ a sensitive laboratory assay method such as mass spectrometry. There are long time intervals spent waiting for testing results from laboratories that use methods such as mass spectrometry. Comparatively, blood testing by finger stick yields the results in 7 to 10 seconds even if there are disadvantages in accuracy.

Thus, there is a need for frequent and accurate self-testing of glucose to extend the life and expand the well-being of these patients. There is also a need to test other associated conditions of metabolic syndrome by means of analyte monitoring in breath. While efforts have been undertaken to increase the ease with which analytes from body fluids, such as glucose, can be periodically monitored, no proposed solution has proved entirely satisfactory that allows convenient monitoring with reduced pain and inconvenience.

SUMMARY OF THE INVENTION

The present invention relates to non-invasive monitoring of analyte concentrations, and more particularly to an integrated breath sampling and detection system for measurement of analytes in breath, breath derived fluids and any other suitable body fluid. The invention discloses a system and method utilizing a handheld continuous volumetric air sampling and extraction (CVASE) device for collection of breath samples, and a system and process of breath analyte measurement to benefit treatment of, for example, human diabetes, metabolic syndrome, obesity, autoimmune disease, infection and related conditions.

The present invention is directed to an apparatus, a cartridge, and a method of using the apparatus and cartridge to detect an analyte.

One embodiment of the invention can be described as an apparatus for detecting the presence of an analyte in a fluid in a cartridge, the apparatus comprising a head assembly and a tail assembly. The head assembly has a photodetector interface configured to cooperate with a sensor port of the cartridge to expose at least a portion of the photodetector interface to a sensor assembly of the sensor port. The tail assembly has an illumination interface, illumination interface configured to cooperate with an illumination port of the cartridge to provide illumination to a portion of the sensor assembly. The head assembly is in clamping relation to the tail assembly such that when a cartridge is disposed between the head and tail assemblies, the head and tail assemblies clamp the cartridge to form a fluidic seal between the illumination interface and illumination port and a fluidic seal between the photodetector interface, sensor assembly, and sensor port. The head and tail assemblies may also form a lightproof seal. In another embodiment, the sensor assembly is only exposed to light from the illumination interface.

In one embodiment, there may be multiple photodetector interfaces and sensor ports. In another embodiment, there may be multiple illumination interfaces and illumination ports. The number of photodetector interfaces and illumination interfaces may be the same or different.

In another embodiment, the apparatus may further comprise a pump configured to move fluid through a cartridge disposed between the head and tail assemblies. In one embodiment, the apparatus may further comprise a processor in electronic communication with the photodetector interface. The processor may be configured to capture analyte detection information from the photodetector interface. In one embodiment, the apparatus further comprises a flow sensor. The processor may be configured to regulate the flow of fluid through the cartridge based on output from the flow sensor.

The invention may also be described as a cartridge for use in an apparatus having a clamping head assembly. The cartridge is configured to detect the presence of an analyte in a fluid. The cartridge may be opaque. In one embodiment, the cartridge comprises a cartridge body, a sensor port, and an illumination port. The cartridge body has an inlet and an outlet. The cartridge body also has a fluid flow-path between the inlet and outlet. The sensor port is on the cartridge body and has a sensor assembly configured to be exposed to fluid in the flow-path. The sensor assembly may be configured to detect glucose, oxygen, or some other analyte. The illumination port is on the cartridge body and is configured to allow light energy to illuminate at least a portion of the sensor assembly in contact with fluid in the flow-path. The sensor port is positioned between the inlet and the outlet, and the sensor assembly is configured to detect the presence or absence of an analyte in the fluid flow-path.

In one embodiment, the illumination port has a filter assembly such that the illumination port is configured to allow the light energy to pass through the filter assembly.

In another embodiment, the cartridge may have a first and second sensor assembly. The first sensor assembly may be configured to detect glucose while the second sensor is configured to detect oxygen, or vice versa. In another embodiment, the cartridge may have multiple sensor ports, sensor assemblies and illumination ports.

In one embodiment, the cartridge further comprises an electronic memory device for storing sensor and calibration data.

The invention may also be described as a method for detecting an analyte in a fluid. The method comprises the steps of clamping a sensor cartridge into a cartridge receiver, providing the fluid in the flow-path, and illuminating at least a portion of the sensor such that at least some portion of the sensor exhibits an optical property, and using the photodetector to detect a change in the optical property. The change may be caused by the presence or absence of the analyte in the fluid.

In one embodiment, the sensor cartridge has a flow path and a sensor configured to be exposed to the fluid when the fluid is present in the flow path. The sensor may be configured to exhibit an optical property when illuminated. The cartridge receiver may have a photodetector configured to detect the optical property of the sensor when the cartridge is clamped in the cartridge receiver.

In another embodiment, the method further comprises the step of using the photodetector to measure a quantity of the analyte in the fluid according to a variance in the optical property.

In one embodiment, the sensor cartridge has a second sensor responsive to a reference analyte and the cartridge receiver has a second photodetector configured to detect the optical property of the second sensor. The method may further comprise the step of using the second photodetector to measure a quantity of the reference analyte in the fluid. In another embodiment, the method further comprises the step of comparing the measured quantity of the analyte according to the measured quantity of the reference analyte.

The invention could also be described as an apparatus for detecting the presence of an analyte in a fluid in a cartridge comprising a head assembly and a tail assembly. Either the head assembly or the tail assembly has a photodetector interface. The photodetector interface is configured to cooperate with a sensor port of the cartridge to expose at least a portion of the photodetector interface to a sensor assembly of the sensor port. In other words, only one of the head assembly or the tail assembly has a photodetector interface, and the other assembly lacks an illumination interface. The head assembly is in clamping relation to the tail assembly such that when a cartridge is disposed between the head and tail assemblies, the head and tail assemblies clamp the cartridge to form a fluidic seal between the photodetector interface, sensor assembly, and sensor port. The cartridge for use in this embodiment may have a cartridge body having a fluid flow-path between an inlet and an outlet, at least one sensor port on the cartridge body, each sensor port having a sensor assembly configured to be in contact with fluid in the flow-path, and at least one light source configured to illuminate at least a portion of each sensor assembly in contact with fluid in the flow-path. The sensor port may be positioned between the inlet and the outlet.

In one embodiment, the cartridge may have a battery in electrical connection with the light source. The cartridge may also have conductive contacts configured to be in electrical connection with the apparatus for delivering power to the at least one light source.

The invention can also be described as an integrated breath extraction and testing system for determining the health of a human patient with diabetes, metabolic syndrome, or related conditions such as infection, autoimmune diseases or obesity. Provided is a Breath analyte monitoring device having a housing, the enclosed device comprising: a means of Continuous Volumetric Air Sampling and Extraction (CVASE);

the CVASE module is capable of insertion in a mechanical ventilator for continuous breath monitoring or is useful as a breath collection module for patients with a condition to be monitored at a user defined time; the housing contains a disposable sensor cartridge that inserts into the air flow channel emanating from the CVASE module; sensors on the cartridge detecting analyte concentrations from breath of human patients, quantifying for example, oxygen and glucose; In another embodiments, oxygen is a reference analyte for definition of breath exposure of the sensor surface. The present device can be directed to monitor other breath analytes indicative of health or diseases including diabetes or metabolic syndrome, and examples include $CO_2$, ketones, urea, creatinine, cytokines including TNF, IL-6 and IL-8, CRP, insulin, GLP-1, PYY, GLP-2, bacteria and components thereof, such as endotoxin, and lactic acid In one embodiment, the device can also be directed to monitor analytes in condensate of breath prepared within the apparatus or the device can be directed to monitor any other body fluid introduced continuously into the sensor cartridge. The process for analyte-sensor quantification includes the preparation of sensor for the analyte to be quantified, the inserted sensor cartridge having configurations for the analyte. The device provides for an optical energy producing source directing optical energy to the sensor surface of the cartridge; the device includes one or more of an electrochemical, amperometric, luminescent, photonic, or other suitable optical energy detector for measurement of voltage or amperage output and a processor for quantification of analyte concentration. In some embodiments, the apparatus and incorporated processor includes an electronic calibration apparatus that provides for sensor calibration; a memory storage device integrated into the sensor cartridge to enable calibration readings and data storage during continuous use. In one aspect, the sensor has an energy source located within the housing, one or more unique analysis sensor surfaces comprising a cartridge preparation, each sensor cartridge adapted to receive breath from the CVASE unit, and one or more light sources adapted to direct light at the analysis sites, one or more light detectors adapted to receive light from the analysis sites, and a processor. The output of the housing and apparatus may be stored and analyzed internal to the housing or sent to an external processing unit for storage and analysis. In one embodiment, the breath glucose concentration measured by the integrated device of the present invention is indicative of a subject's immediate glycemic condition. In another embodiment, the breath analytes measured in addition to oxygen and glucose are indicative of diabetes, obesity, metabolic syndrome and complications thereof. The present invention also provides a means of diagnosing diabetes and metabolic syndrome, or aspects thereof.

BRIEF DESCRIPTION OF THE DRAWINGS

For a fuller understanding of the nature and objects of the invention, reference should be made to the accompanying drawings and the subsequent description. Briefly, the drawings are:

FIG. 5B is a diagram of one embodiment of a continuous liquid flow sensor cartridge having two channels according to the present invention;

DETAILED DESCRIPTION OF THE INVENTION

Figure 13:
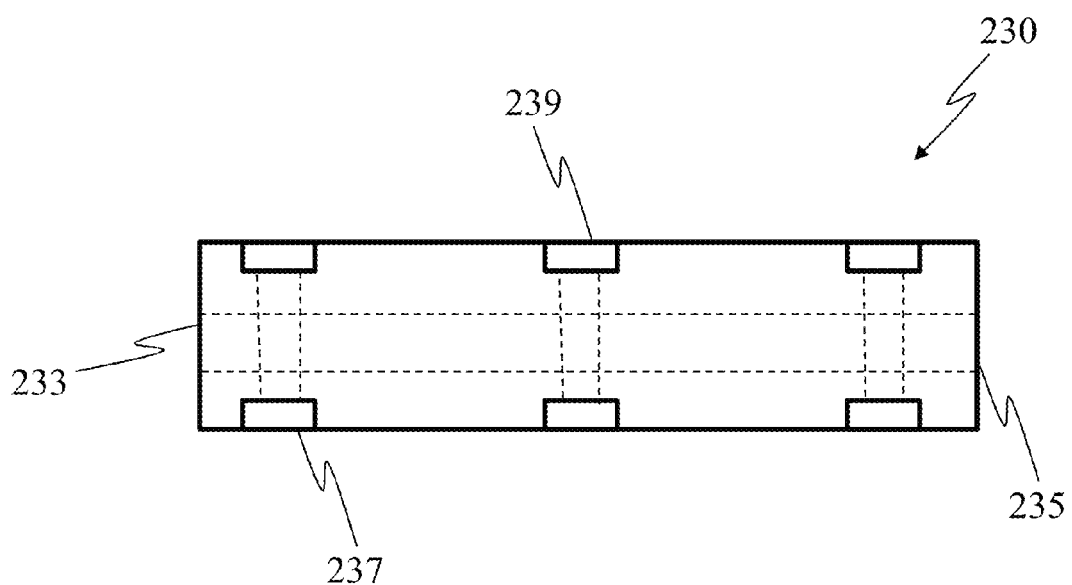
FIG. 13 is a diagram showing a cartridge according to one embodiment of the present invention.

The present invention can be described as an apparatus 200 for detecting the presence of an analyte in a fluid in a cartridge 207. FIG. 13 shows a diagram of one such embodiment. As used herein, the term "fluid" refers to a liquid, gas, or combination of both liquid and gas. An analyte, for example, may be glucose, oxygen, or any other molecule present in the liquid.

In one embodiment, the apparatus 200 comprises a head assembly 201 and a tail assembly 203. The head assembly 201 or tail assembly 203 may be formed from any suitable material, including for example, plastic, metal, or a combination of materials.

The head assembly 201 may have a photodetector interface 205. The photodetector interface 205 may comprise a CCD or CMOS sensor, photodiodes, or some other optical detector. The photodetector interface 205 is configured to cooperate with a sensor port 209 of a cartridge 207. For example, the photodetector interface 205 may be mechanically formed to removably mate with the sensor port 209. In another example, the photodetector interface 205 may have a gasket, o-ring, or other type of seal in order to create a fluidic and/or lightproof seal, thus preventing external light or fluid from entering the sensor port 209. The photodetector interface 205 is configured to be exposed to at least a portion of a sensor assembly 217 of the sensor port 209. In this way, a response emitted by the sensor assembly can be detected by the photodetector interface 205.

The tail assembly 203 has an illumination interface 211. The illumination interface 211 may have an LED or some other light-producing component. The illumination interface 211 is configured to cooperate with an illumination port 213. For example, the illumination interface 211 may be mechanically formed to removably mate with the illumination port 213. In another example, the illumination interface 211 may have a gasket, o-ring, or other type of seal in order to create a fluidic and/or lightproof seal, thus preventing external light or fluid from entering the illumination port 213. The illumination interface 211 is configured to provide illumination to a portion of the sensor assembly in the sensor port 209. The illumination interface 211 may be configured (along with the cartridge 207) such that only light from the illumination interface 211 reaches the sensor port 209. In embodiments where there are multiple illumination interfaces or multiple sensor ports, the illumination interfaces may be configured to illuminate one or more of the sensor ports. For example, there may be a one-to-one relationship between an illumination interface 211 and a sensor assembly 217 of sensor port 209 or a one-to-many relationship between an illumination interface 211 and more than one sensor assembly.

The head assembly 201 is in a clamping relation to the tail assembly 203. For example, the head assembly 201 may be mechanically coerced to move toward the tail assembly 203. Alternatively, the tail assembly 203 may be mechanically coerced to move toward the head assembly 201, or both the tail assembly 203 and the head assembly 201 may be mechanically coerced to move toward each other. When a cartridge 207 is disposed between the head assembly 201 and the tail assembly 203, the assemblies 201, 203 clamp the cartridge 207. When the cartridge 207 is clamped, a fluidic seal is formed between the illumination interface 211 and the illumination port 209. Also, a fluidic seal is formed between the photodetector interface 205 and the sensor port 209. The sensor assembly (not shown) may be positioned in between the photodetector interface 205 and the sensor port 209 in such a way that does not compromise the fluidic seal. The fluidic seals between the interfaces and ports may also be lightproof.

In one embodiment, either the head assembly or tail assembly may have a photodetector interface. There may be multiple photodetector interfaces in this embodiment. A cartridge for use with this embodiment may have an internal light source configured to illuminate at least a portion of each sensor assembly. In other words, the illumination interface is moved from the head or tail assembly to the cartridge. The cartridge may also comprise a battery to power the internal light source or, the cartridge may have electrical contacts such that the light source can draw power from the apparatus when the cartridge is inserted.

In another embodiment, the apparatus 200 may also comprise a pump. The pump may be configured to move fluid through the cartridge 207. The pump may be configured to provide a constant flow of fluid, or the pump may be configured to vary the rate of flow. The pump may rely on flow sensors, temperature sensors, or the information from the sensor assemblies to regulate the rate of flow.

In one embodiment, the apparatus 200 may further comprise a processor. For example, the processor may be a general purpose CPU, a low-power CPU, or a suitable microprocessor. The processor may be in electronic communication with the photodetector interface 205. The processor may be configured to capture analyte detection information from the photodetector interface 205. For example, the processor may capture data about the magnitude or wavelength of light being emitted from a sensor assembly. The processor may analyze successive readings in order to determine an average or change in a sensor assembly's optical property.

In another embodiment, the apparatus 200 may further comprise a condenser. The condenser may be configured to change the phase of the fluid to a liquid from a gas. Likewise, an evaporator may also be provided and configured to change the phase of the fluid to a gas from a liquid. The condenser and evaporator may be used to ensure that the fluid is a single phase.

The present invention can also be described as a cartridge 230 for use in an apparatus 200. The apparatus may have a clamping head assembly, for example, the head and tail assemblies described above. The cartridge 230 is configured to detect the presence of one or more analytes in a fluid. The cartridge 230 may be opaque. The cartridge 230 has a fluid flow-path 231 between an inlet 233 and outlet 235. The cartridge 230 also has at least one sensor port 237 and at least one illumination port 239. Each sensor port 237 has a sensor assembly. The sensor assembly is configured to be exposed to fluid in fluid flow-path 231. The sensor assembly is configured to detect an analyte by emitting a signal. Some analytes that may be detected include, but are not limited to, glucose and oxygen. For example, the optical characteristic of the sensor assembly may change in the presence of an analyte. In another example, an optical response may be generated when light energy is applied to the sensor assembly and the sensor assembly is in the presence of an analyte. The illumination port 239 is configured to allow light energy to illuminate at least a portion of the sensor assembly in contact with the fluid flow-path 231. The sensor port 237 is positioned between the inlet 233 and the outlet 235.

In another embodiment, the illumination port 239 has a filter assembly such that the illumination port 239 is configured to allow light energy to pass through the filter assembly. The filter assembly may be clear and allow all light to pass. The filter assembly may also filter out predetermined wavelengths such that only a narrow wavelength band of light passes through the filter. The filter may also filter out different polarizations of the light.

In one embodiment, the cartridge 230 has a first sensor assembly and a second sensor assembly. The first and second sensor assemblies may be configured to detect the same analyte, or they could be configured to detect different analytes.

In another embodiment, the cartridge 230 may further comprise an electronic memory device for storing sensor and calibration data. The memory device could be a chip or a removable card.

The present invention may be embodied as a method 500 for detecting an analyte (an "analyte-of-interest") in a fluid. The fluid may be any fluid, including, without limitation, a bodily fluid. It should be noted that, as used herein, fluid may be a gas, a liquid, or combination of both. In some embodiments, the fluid may be a liquid which was condensed out of a gas.

Figure 11:
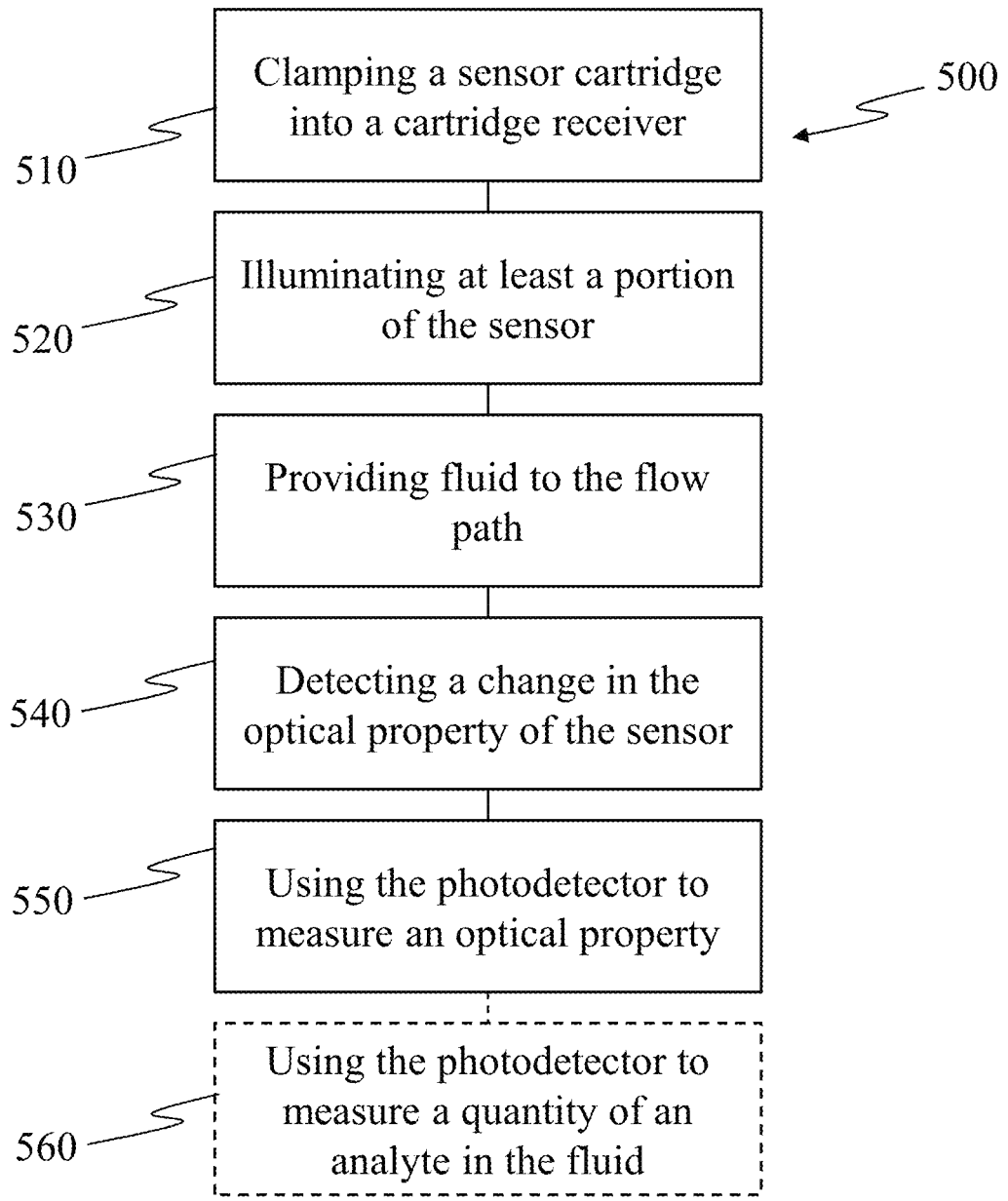
FIG. 11 is a flowchart showing a method according to one embodiment of the present invention.
Figure 12:
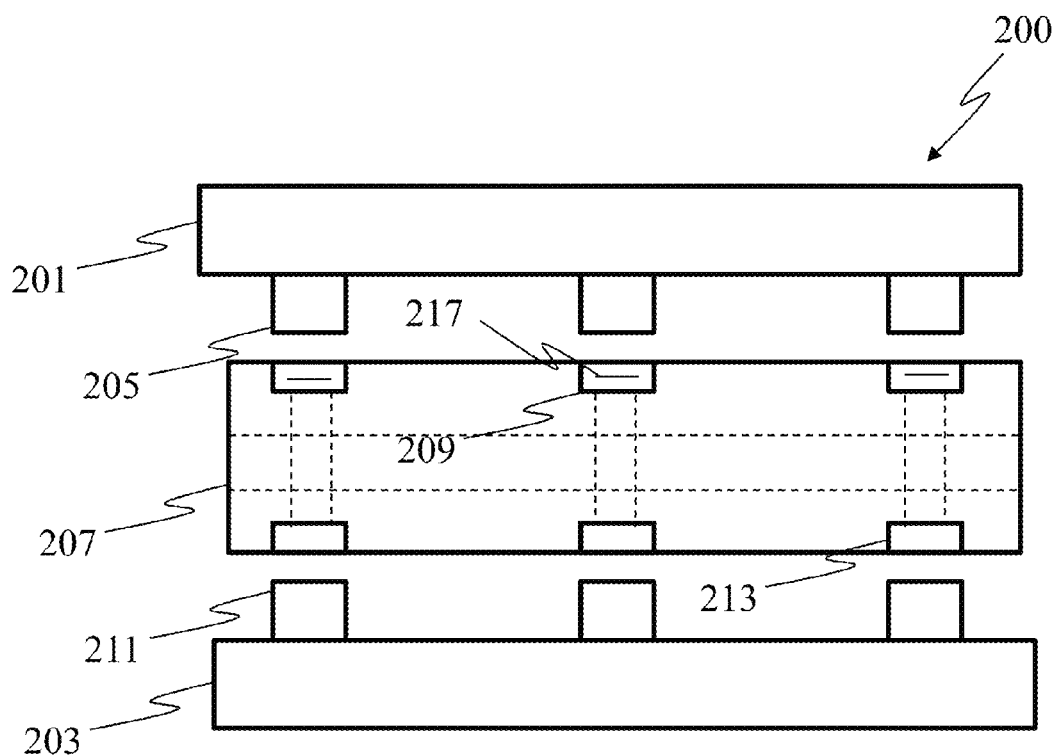
FIG. 12 is a diagram showing an apparatus according to one embodiment of the present invention.

FIG. 11 is a flow chart showing a method 500 according to one embodiment of the present invention. The method 500 comprises the step of clamping 510 a sensor cartridge into a cartridge receiver. The sensor cartridge may be configured, for example, as described elsewhere in this disclosure. The sensor cartridge had a flow path through which the fluid can flow. The sensor cartridge has a sensor configured such that the sensor is exposed to the fluid when the fluid is in the flow path. The sensor of the sensor cartridge exhibits an optical property when illuminated. And the sensor is responsive to the analyte of interest by way of changes in the optical property.

The cartridge receiver has a photodetector which is configured to detect the optical property of the sensor when the sensor cartridge is clamped in the cartridge receiver.

The method 500 further comprises the step of illuminating 520 at least a portion of the sensor, causing the sensor to exhibit the optical property. As described in this disclosure, the source of the illumination may be part of the sensor cartridge or the cartridge receiver.

Fluid is provided 530 to the flow path. The fluid may be continuous flow (e.g., continuously moving) or the fluid may be still for a short or long period of time.

The photodetector is used 540 to detect a change in the optical property of the sensor. As described above, the optical property changes depending upon the presence or absence of the analyte of interest. As such, the photodetector is used to detect the presence or absence of the analyte in the fluid.

The sensor may be configured to be variably responsive according to a quantity (e.g., volume, concentration, etc.) of analyte in the fluid. For example, the sensor may have an optical property which is capable of incremental change according to the quantity of analyte. In another embodiment, the sensor is comprised of a plurality of subsensors and the sensor has a variable response according to the ratio of the number of subsensors having an optical property in a first state (e.g., absence of analyte) compared to the number of subsensors having an optical property of a second state (e.g., presence of analyte). The method 500 may thus comprise the further step of using 550 the photodetector to measure a variance in the optical property of the sensor to determine a quantity of the analyte in the fluid.

The sensor cartridge may have a second sensor which is responsive to a second analyte, which may be a reference analyte. In this way, the method 500 may further comprise the step of using the photodetector to measure a quantity of the reference analyte. The reference analyte may be selected such that the value of the analyte of interest can be corrected or normalized 560 according to the value of the reference analyte. Accordingly, the method 500 may further comprise the step of normalizing the measured quantity of the analyte (the analyte of interest) according to the measured concentration of the reference analyte.

The following discusses one or more exemplary embodiments of the present invention.

In order to overcome these limitations in accuracy and detection, an optical methodology for measurement of glucose is adapted to use on a handheld device, and this method incorporates an improved means of standardizing the breath to breath variability of previous methods by means of a previously disclosed oxygen sensor as a reference for the breath glucose concentration. Additionally, the methodology of continuous volumetric air sample extraction (CVASE) was used in place of the difficult to standardize method of exhaled breath condensate. The use of CVASE allows for the accurate measurement of glucose in each breath while the patient was breathing normally at rest. The combination of oxygen as a reference standard and CVASE allowed for accurate measurement of glucose in each breath during the breathing pattern of the human subject at rest. The use of the improved optical sensor for glucose allowed the detection of breath glucose without the need of condensing the breath sample or altering it in any way. The application of all three of these features results in a working handheld glucose breath testing device which is robust, reliable and more accurate than methods used for either blood glucose measurement or breath glucose measurement in conventional practice. Many other standard features of optical detection needed improvement in order to reproducibly and reliably measure breath glucose and those features will also be disclosed as system embodiments in the use of glucose monitoring for patients with diabetes.

It will be readily apparent to those skilled in the art of measurement of glucose in breath, that the device which uses CVASE and optical detection can also be used to measure other breath analytes, and in fact can measure any analyte that can be measured in blood, so long as it is possible to develop an optical measurement sensor surface for the analyte on the device disclosed herein.

It will be readily apparent to those skilled in the art of measurement of any body fluid, that the device which uses a pump to control flow rate of presentation to sensor surface and optical detection can also be used to measure analytes from blood, urine, saliva, microdialysis fluid, bile, cerebrospinal fluid, gastrointestinal fluid, or vaginal fluid, and in fact the CVASE principle can measure any analyte that can be measured in blood, so long as it is possible to develop an optical measurement sensor surface for the analyte. Additional detection systems and/or additional reference analytes can be incorporated into the device.

Provided here is a reliable and essentially pain-free approach to frequent glucose monitoring, or for monitoring of any blood component which is also found in breath. The use of very small samples of breath as withdrawn by CVASE, combined with a sensitive and reliable chemical test for glucose or the target analyte in an automated device allows for metabolite monitoring with immediacy, convenience, and complete comfort. If the methodology is applied to the breath stream from a mechanical ventilator device or similar life sustaining instrument, the automation of the glucose and oxygen testing offers an inherent psychological advantage in that the occurrence of the testing is essentially unknown to the user. Automation offers a further advantage in that a specific program can be applied for frequent testing based on the user's needs for treatments. With the present invention, a large number of tests can be performed; for example glucose and oxygen tests every 2 minutes for up to 7 days can be provided per manufactured sensor unit, thus allowing frequent testing over times of serious illness in the intensive care unit. For use by patients desiring monitoring of their diabetes, the added features of small size, accuracy and the convenience of breath testing would allow for testing on a frequent basis over the course of a day and the long life of the sensor cartridge allows testing of glucose for one week from each sensor cartridge. Furthermore, miniaturization allows for the design of a small breath testing device that can be carried everywhere by the patient and can be used to test many analytes and communicate this information to caregivers.

Figure 1A:
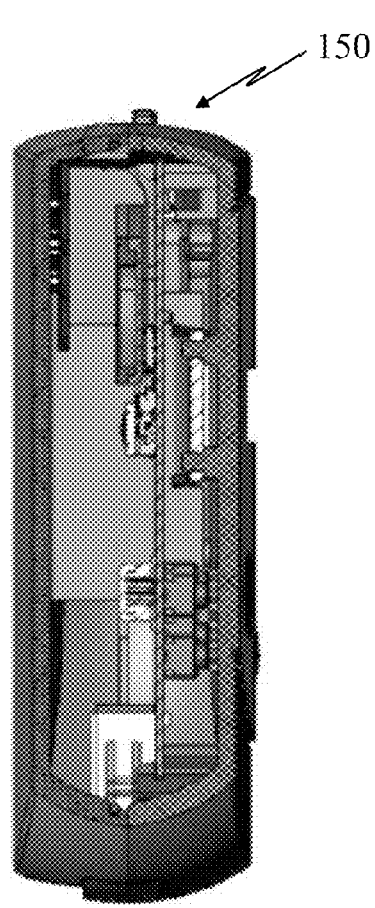
FIG. 1A is a side view of one embodiment of a breath testing apparatus according to the present invention.
Figure 1B:
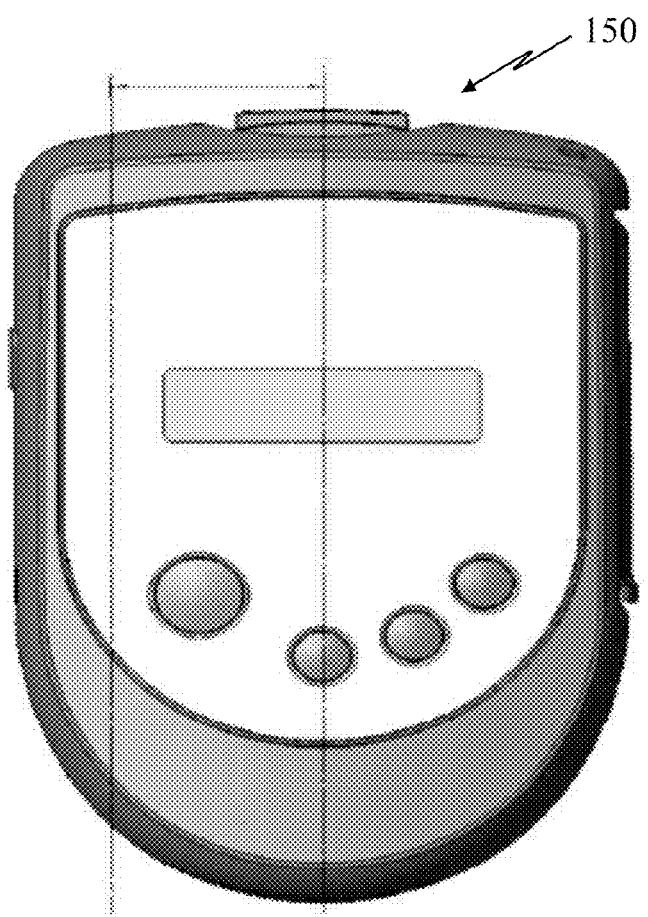
FIG. 1B is a front view of the embodiment shown in FIG. 1A.

The following refers to FIG. 1A and FIG. 1B, a generalized external diagram of one embodiment of the apparatus, side view and front view, respectively. The diagrams are intended to identify the major external components of one of the embodiments 150 of the present invention. A generalized block diagram of one embodiment of the apparatus is shown as FIG. 2. The analyte sensing system is comprised of Light Emitting Diode (LED) drive and signal processing circuit (1 in FIG. 2), two LEDs (2 & 3 in FIG. 2) the output wavelength (color) of which is determined by the stimulus wave length required by the sensor to fluoresce if the desired analyte is present. For example, two LEDs having a peak wavelength output of 470 nm (blue) are used to stimulate emissions in the 600-650 nm range for a sensor formulated to detect glucose and oxygen presence in breath or liquids.

In one optical excitation circuit, two or more LEDs are used, with provisions for alternative optical inputs from lasers in one or more of the excitation channels. Provisions for two or more excitation channels facilitate use of a reference channel and one or more sensor channel(s) for the measurement and quantification. The sensor channels can elucidate responses from, by way of example, photodiodes, CMOS or photomultiplier optical detectors. In the case of sensors formulated to monitor glucose the reference channel sensor will contain a sensor formulated to monitor oxygen while the sensing channel contains a sensor formulated to monitor oxygen and glucose, the method using the measurement of the reference channel to quantify the glucose response of the sense channel. When used with additional analytes these photodiodes may be photomultipliers or CMOS detectors with consideration of the needs of the accurate capture of output signal from the sensor surface. In one embodiment for measurement of glucose oxidase enzymatic action on substrate glucose, the optical pathway is a direct channel of 180 degrees with excitation optimized to 470 nm and filters optimized for emission at 600 nm. For analytes with less optimal stokes shifts between excitation and emission, the channel angle for the optical pathway may be other than 180 degrees, specifically 30-45 degrees, 90 degrees, or 210-230 degrees in order to provide bypass photonic input to the sensor.

The analyte sensing system also contains two photodiodes (4) that are optically coupled to the LEDs (2 & 3). Optical coupling is achieved using a fiber optic or prism coupling means. The detected light output from these sensors is processed by the Light Emitting Diode (LED) drive and signal processing circuit (1 in FIG. 2) providing light intensity feedback for both detection channels. This feedback is used to maintain the LED output intensity at optimal values for analyte measurement, keep the LED intensity stable during the measurement period and extend the sensor life by limiting the optical bleaching effect on the sensors.

The sensors are contained in a disposable cartridge (5) inserted between the LEDs and main photo detectors (6 & 7). The arrow through the center of the cartridge (5) indicates the direction of flow of breath or a liquid over the active face of the cartridge in the case of a breath based system or for a liquid through the cartridge for a liquid based system. The sensing cartridge also contains a Flash memory chip (11 in FIG. 2) that is used to store factory calibration data for the sensors, a 32-bit unique electronic serial number that contains manufacture date and lot number and a counter representing the number of times the sensing cartridge has been used or accessed. This flash memory also contains the sensor data from the last 25 cartridge measurements. Additional memory within the microprocessor and or an external Flash memory chip is also used to store measurement and performance data for the device. Two high sensitivity photo detector diodes (6 & 7) are used to measure the sensors' output. The signals from these sensors are amplified and filtered by the Light Emitting Diode (LED) drive and signal processing circuit (1 in FIG. 2) and then passed to the microprocessor (8) for digitization, normalization and processing to create a measured value of detected analyte. Additional detail of the sensing system and sensing cartridge can be found below following FIG. 3.

In one embodiment, all of the device's peripherals control, signal processing, communications, self test and smart power system functions are accomplished using microprocessor (8). This microprocessor is characterized as a low power feature rich device such as the MSP430™ series processors from Texas Instruments. With general reference to the external diagram in FIG. 1, the peripherals include; a custom Liquid Crystal Display LCD (14) (color or monochrome), a four button user interface (16), an audio indicator (17) (buzzer or tone), a USB 2.X interface (9), a 802.xx wireless interface (10) (Bluetooth or other protocol), a tri color LED indicator (18) for sample validity, Flash memory (20), smart power system (19) and a pump driver and pump (12 & 13, respectively) supporting the CVASE sampling system. The function of each of these peripherals is described below.

The LCD (14) is a custom display containing specialized icons, large font text support and a black light. The display is used to provide instruction for the user covering basic device function and use, displaying system status and display of both historic and current measured data. The last 10 to 50 of the system's internal self test results are stored in flash memory (20) and can also be displayed. Intensity of the LCD Backlight (15) is user adjustable in order to accommodate device use in a wide range of ambient lighting conditions.

The four button user interface (16) is supported by both a "Soft Key" interface and a classic four button menu system. The "Soft Key" interface uses the LCD display to indicate assigned key function. The menu system provides a classic four button user interface where the button functions are "MENU" Key, "SELECT" Key, "UP" Key and a "DOWN" Key. The LCD (14) also displays icons which map the button function for the user. Audio and tactile button press feedback provides reassurance to the user that button press was recognized.

By combining all of the above User Interface hardware (individually, 14, 16 & 17) with software input error checking and contact de-bounce filtering and intuitive select function will produce a user interface that is simple to use, reliable, less prone to input errors and less frustrating for a typical user than most currently available hand held devices.

The audio indicator (17) may be a buzzer of the fixed frequency type or a small piezo device for multiple tone use. Audio is used to provide user feedback representing a valid user input, to draw user attention to a system status message displayed on the LCD (14) and as an indicator of proper device use. An example of the latter would be in a breath sampling system where a short "chirp", from the audio indicator would indicate completion of a proper breath cycle.

Two communication interfaces are provided in one embodiment of the device: a wired Universal Serial Bus (9) (USB) compliant with USB 2.X connector and a wireless interface (10) compliant with 802.xx specifications. The wired USB interface (9) connector is designed to mate directly with a Personal Computer (PC) for transfer of stored data, software updates etc. The wireless communication interface (10) Provides file transfer via a wireless 802.xx compliant data link. Both interfaces are supported by the microprocessors (8) Universal Asynchronous Receiver/

Transmitter (UART) serial interfaces. There are many communications protocols that may be used for this interface. One example would be a BlueTooth™ interface which provides support for cell phone applications to monitor stored data as well as establish BlueTooth™ connectivity to a BlueTooth™ enabled PC or other device. All data transmitted or received via the wireless or wired interface is encoded to insure a secure communication channel in accordance with current HIPAA requirements.

The Tri-Color LED indicator (18) is a multi-purpose indicator that provides user feedback during operation as a breath analyte sensing device. In this mode the indicator signals the user that the device is ready to analyze a breath cycle and that the breath input was valid for the measurement. Software is used to gauge the quantity and velocity of the breath cycle to determine its validity for measurement. This indicator also provides data status for wireless data transmission from/to the 802.xx (9) module. The indicator is also used to indicate a Pass/Fail condition resulting from device self test.

One embodiment for this invention contains an embedded Flash memory chip (20) for data storage of test results and self test results. Alternatively, a portion of the memory for the microprocessor could be used for this purpose. However, the amount of memory available for this function would be limited and the stored data lost if it is not transferred via one of the communication interfaces to a PC or written to the cartridge (5) Flash prior to removing power from the device.

Power for the device is supplied by either primary alkaline or coin cell type batteries (19) or by a single Li-ion secondary (rechargeable) chemistry type cell or by a power adapter using mains power (110, 220 VAC). Ideally the battery voltage would be in the range of 3.4 to 6 volts. The system employs a series of switching and low noise voltage regulators forming a smart power system (21). This system includes a true Battery capacity monitor (Battery Fuel Gauge) providing an accurate representation of remaining battery capacity (hours of operation). Capacity is displayed on the LCD (14) using a custom icon. The microprocessor determines which of its peripherals are required at any given time during normal operation and activates only the voltage regulators for the peripherals required to perform the selected task. This in conjunction with the multiple power modes for the microprocessor (8) produces a smart power system which maximizes battery life.

The CVASE sampling system is supported by a discrete pump driver (14) circuit controlled by a Pulse Width Modulated (PWM) output from the microprocessor (8). Pump (13) provides a fixed sample size to the analyte sensor (5) and in the case of a breath based sensing system removes excess condensate from the sample. Pump speed is software controlled and is automatically adjusted to produce an adequate sample size for the sensors. The pump is capable of moving both gaseous and liquid based sample media.

Figure 2:
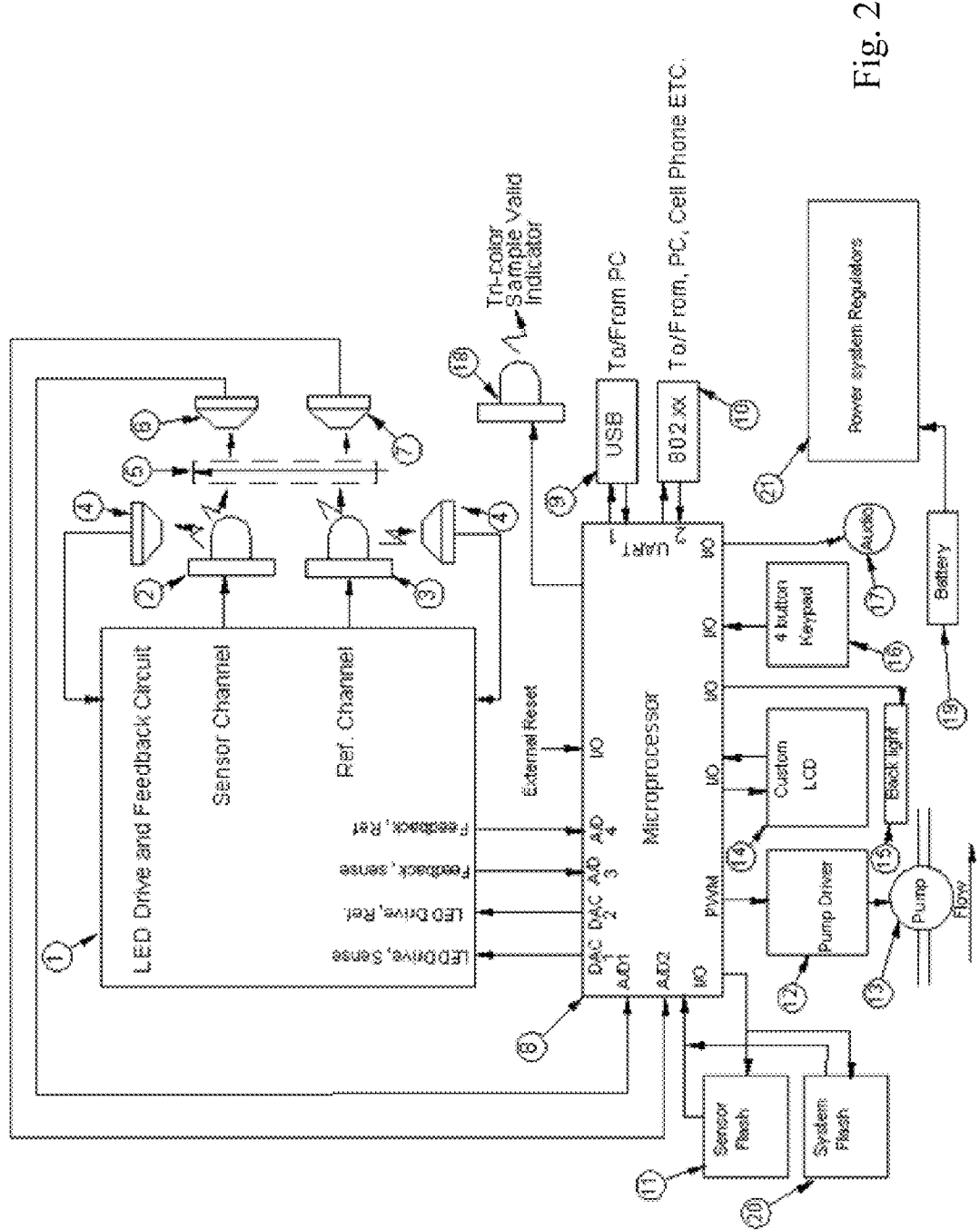
FIG. 2 is a system block diagram of one embodiment according to the present invention.
Figure 3:
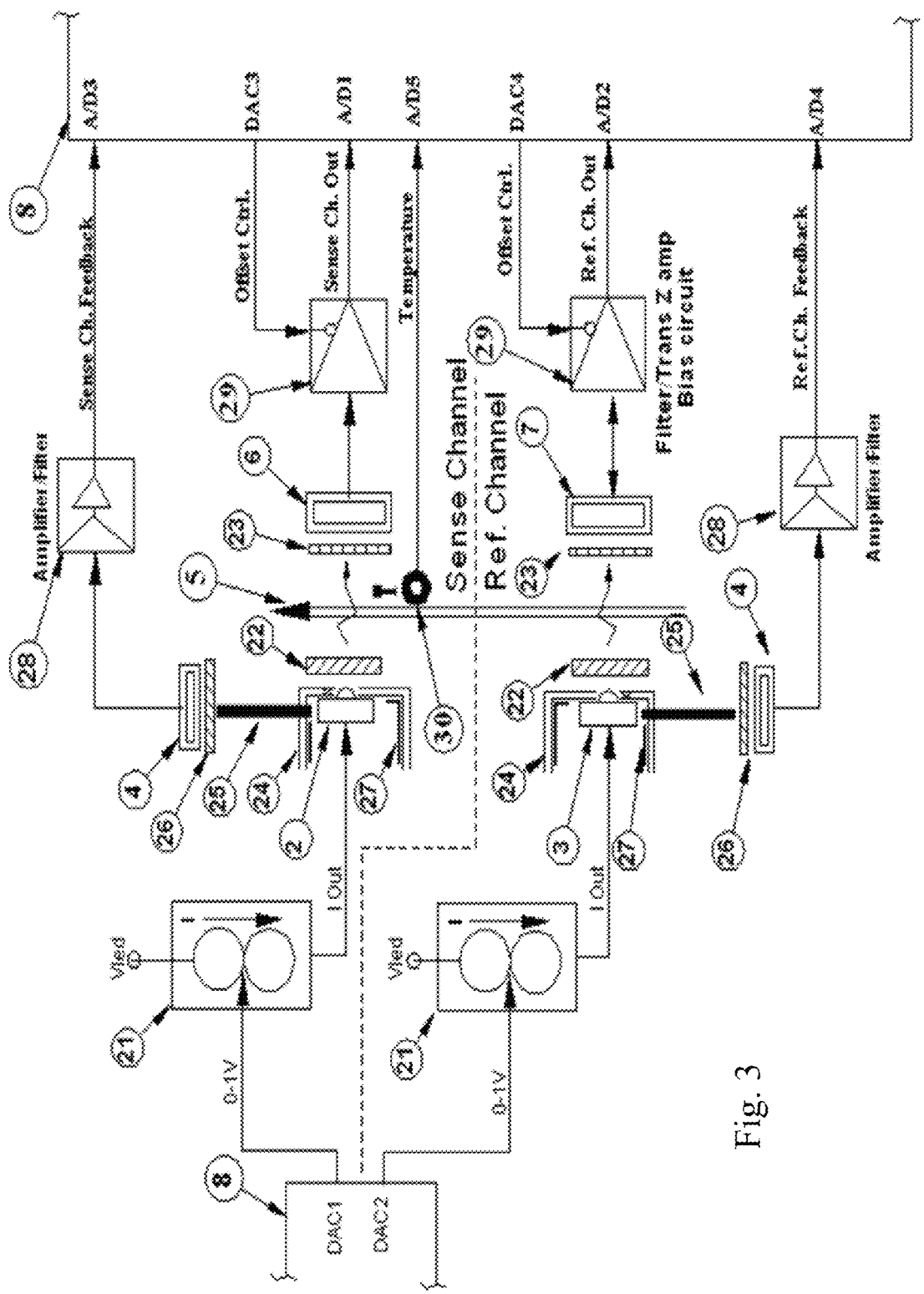
FIG. 3 is a schematic representation of an optical sensing circuit used in one embodiment according to the present invention.

FIG. 3 is a schematic representation of one of the embodiments for the two channel analyte detection system (1-7 in FIG. 2). This detection supports the CVASE sampling system and disposable cartridge type sensors (5 in FIG. 3) for both gases, breath for example or liquid sample media. The circuit topology provides automatic correction of light intensity for both sensing channels, accurate, stable and repeatable current drive for the LEDs, photo detector bias and output amplification, digital photo detector output signal base line correction and filtering.

Light sources (2 & 3) direct optical energy of a specific wave length designed to excite the sensor in the presence of a specific analyte through a mask (27) pin hole and LED support (24) sensor cover (22). This light energy is focused on the sensors which are located accessible to the optical path. Out of band radiation from the sensor and light source are removed by color filter (23) which is a transmissive design. Energy transmitted through this filter is detected by a photo diodes (7 & 6), amplified and scaled by (29) and digitized by microprocessor (8). The electronics supporting both measurement channels is the same. Light intensity from the LEDs is controlled using an optical feedback loop and amplifier. This circuit comprises fiber optic sampling (25) of the LED intensity, a light source filter (26) and photo detector (4) again both measurement channels use the same components and configuration. Out of band light (color other than LED color) from the optical fiber is filtered using a transmissive filter (26). Feedback photo detector (4) output is amplified and scaled by (28) and digitized by the microprocessor. LED intensity is accurately and repeatability controlled using two high resolution temperature compensated programmable current sources (21) controlled using the digital to analog converter outputs of the microprocessor (8). A temperature sensor (30) is located near the cartridge (5) sensors and thermally coupled to the fluid path. The output of this sensor is digitized by the microprocessor (8) and used to adjust the sensor calibration for temperature and as part of the algorithm used to determine the validity of a breath input.

Figure 4A:
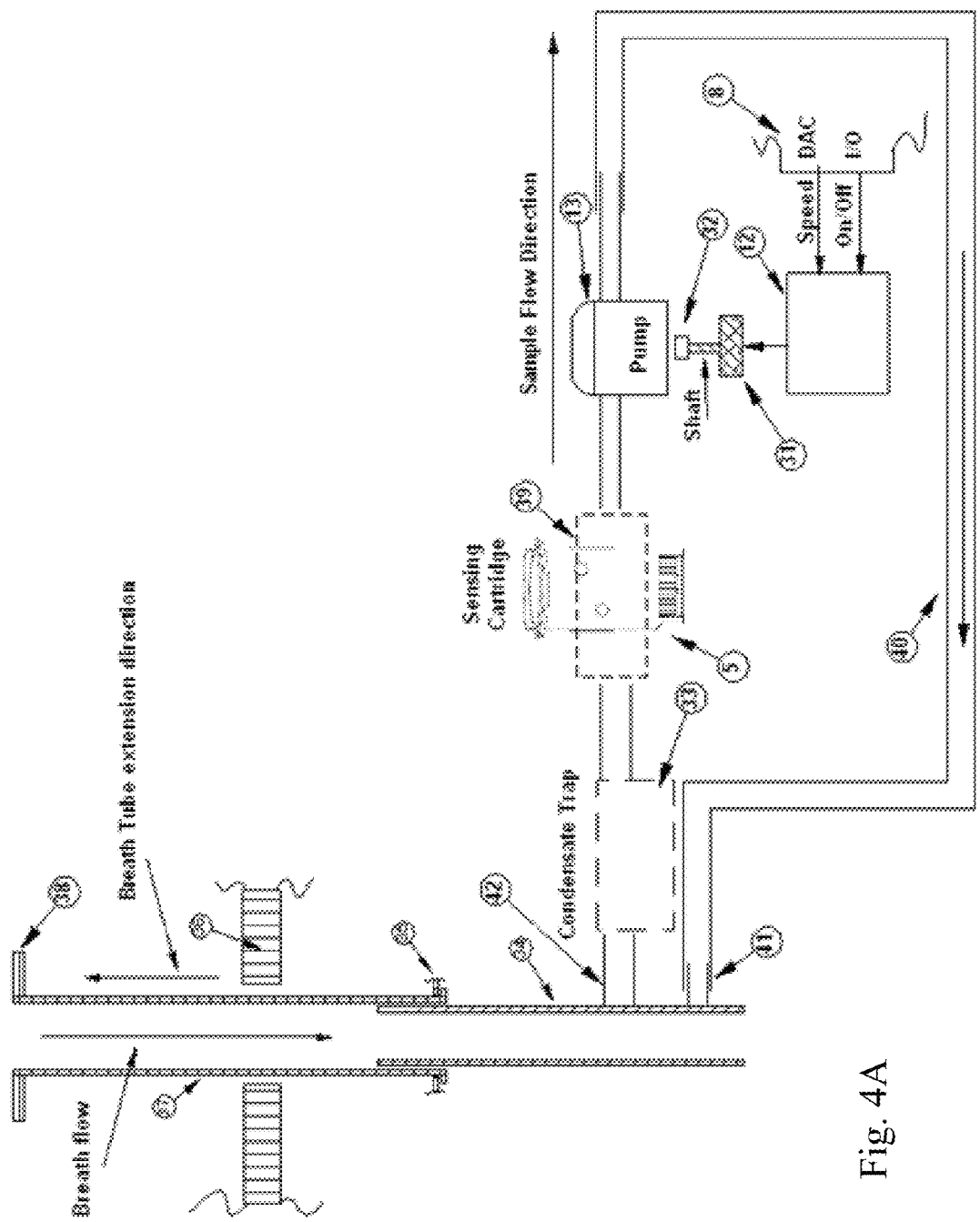
FIG. 4A is a diagram of one embodiment of a CVASE apparatus having a 2-channel glucose breath testing cartridge according to the present invention.
Figure 4B:
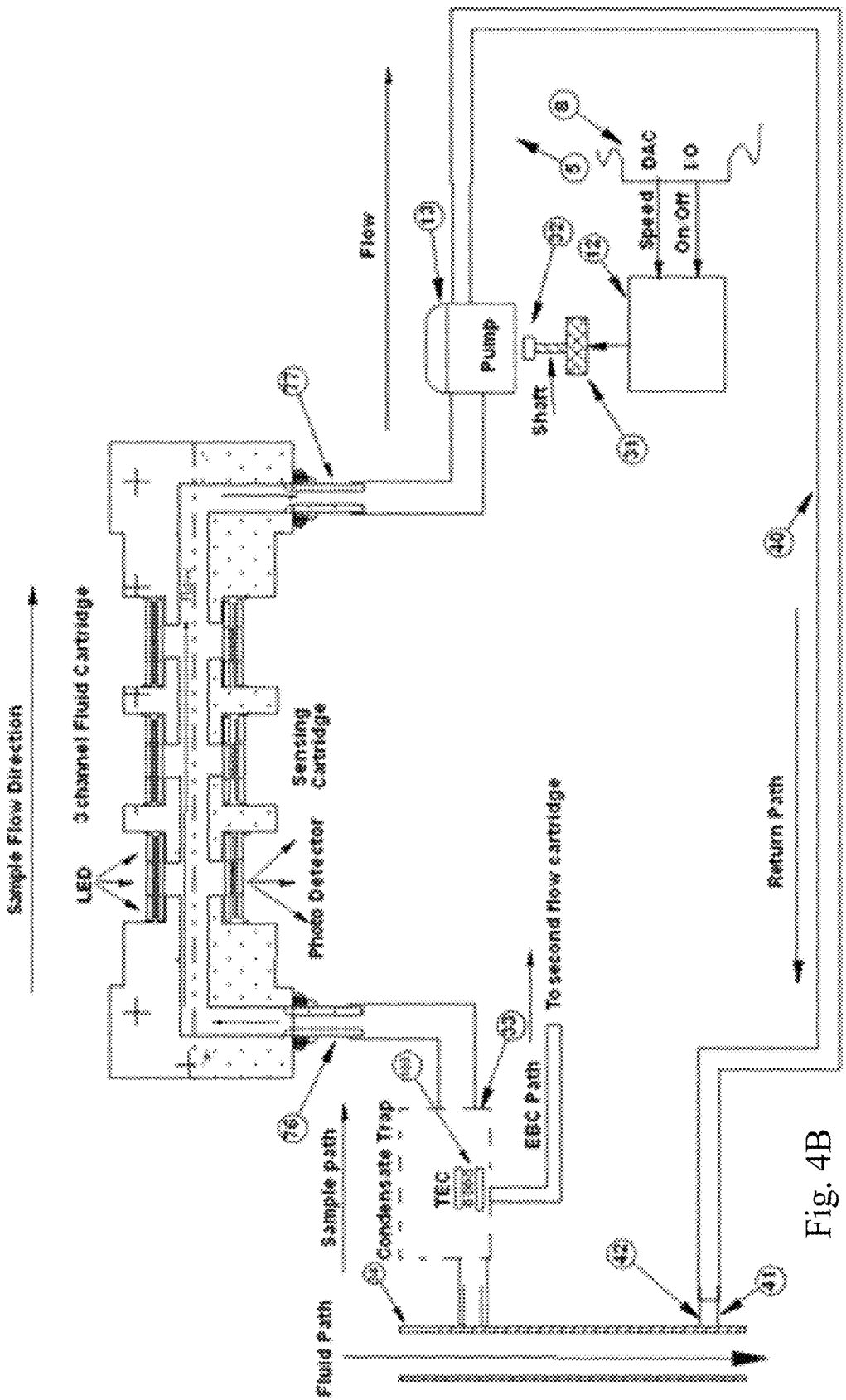
FIG. 4B is a diagram of another embodiment of a CVASE system having a 3-channel sensing cartridge and a thermoelectric cooler (TEC) according to the present invention.

FIGS. 4A and 4B illustrate two embodiments of the Continuous Volumetric Air Sampling and Extraction (CVASE) apparatus. The CVASE method enables the reliable quantification of breath concentrations of analytes. CVASE uses a pump to regulate and control the rate of presentation of a breath sample to the sensor. In one embodiment, the rate of sample presentation to sensor surface by CVASE is directly proportional but not equal to the entire breath stream. In this manner variations in rate of breathing or force of exhale or inhale are controlled for as they are used in the interpretation and quantification of sensor output. The CVASE system operation is controlled by the microprocessor using the output of the reference channel of the optical sensing system response and the temperature sensor (30, FIG. 3) response to control the sampling pump (13, FIG. 4A) speed. The component configuration in FIG. 4A illustrates an embodiment of the CVASE system designed to support analysis of breath using a two channel sensing cartridge. FIG. 4B illustrates an embodiment of the CVASE system designed to support analyte detection in any fluid. A three channel sensing cartridge is used in this configuration.

An example using this system to sample analyte in breath follows; the process of CVASE sampling begins when the breath tube (37) is extended from the side of the case (36) until it reaches the stops (35) built into the case of the handheld meter. This tube is supported by the sterilize-able support tube (34) with ports (42 & 41) which function as a sample input port (42) and a sample return port (41) having a sample return path (40). The sample return port (41) is not used in some of the sensing cartridge configurations. If the return port is not used then the sampled air stream is exhausted to the room. The cartridge sample flow channel (39) is indicated using a dashed line covering the active face of the sensing cartridge. The design of this assembly varies with each cartridge type additional detail is provided below. This action or a button press on keypad (16, FIG. 2) causes the device to begin a breath measurement cycle.

Baseline values for temperature (30) and the optical reference channel are established. If, by way of example an oxygen sensor is used in the reference channel its baseline value would represent ambient oxygen levels in the area where the measurement is to occur. The microprocessor (8) sets the pump speed at a nominal value for this measurement. Once baseline values have been established the meter will indicate via LCD (14) and audio indicator (17, FIG. 2) that it is ready for a breath measurement. The signal is given for the subject to breath normally into the disposable breath tube (37) mouth piece (38) and the CVASE apparatus continuously samples from this breath stream created by the action of pump (13). The sampled breath passes in a regulated manner through optional disposable partial condensate trap (33) and is then directed into the measurement cartridge (5). The disposable partial condensate trap is not required some types of cartridge based sensing systems (see FIG. 4A). The condensate trap may also incorporate a solid state Thermal Electric Cooler device (103, FIG. 4B) to heat the sampling media, thereby preventing condensation in breath or alternatively cooling the fluid to create Exhaled Breath Condensate (EBC) for analysis. The change from baseline value for temperature sensor (30, FIG. 3) cycle signals the start of a breath cycle. The response of the oxygen sensor in the reference optical sensor path (decrease from baseline value) is used to control the pump (13) speed until stable measurement values are achieved. Pump driver circuit (12) contains the power electronics necessary to drive the pump. The change from baseline values for both the reference and analyte specific channels of the sensor cartridge are illustrated later in the description.

The filtered optical output of the sensor surfaces reaches the surfaces of the PDs below the cartridge. These optical signals are converted to voltage outputs by the PDs and are then monitored to produce a quantifiable analyte measurement. The rotor and body of the pump (13) is designed to be disposable and is magnetically driven by motor (31) which has a drive magnet (32) attached to its shaft. In some embodiments, the rotor of the pump would be placed within the sensor cartridge near the exit port. The embodiment illustrated in FIG. 4B uses an adapter tube (34) to couple to a device producing a fluid stream for analysis. For example, the tube could be configured to adapt to a patient ventilator to monitor oxygen levels and other analyte expelled by the patient or the tube could be configured to attach to a patient urine trap to continuously monitor components of the expelled urine. The three channel cartridge drawn in FIG. 4B couples to the sampling system using input port (76) and output port (77).

FIGS. 5A through 5H illustrate possible embodiments for the disposable sensing cartridge and means to achieve a stable connection and secure interface with permanent components, and replaceable mounting within the system apparatus.

Figure 5A:
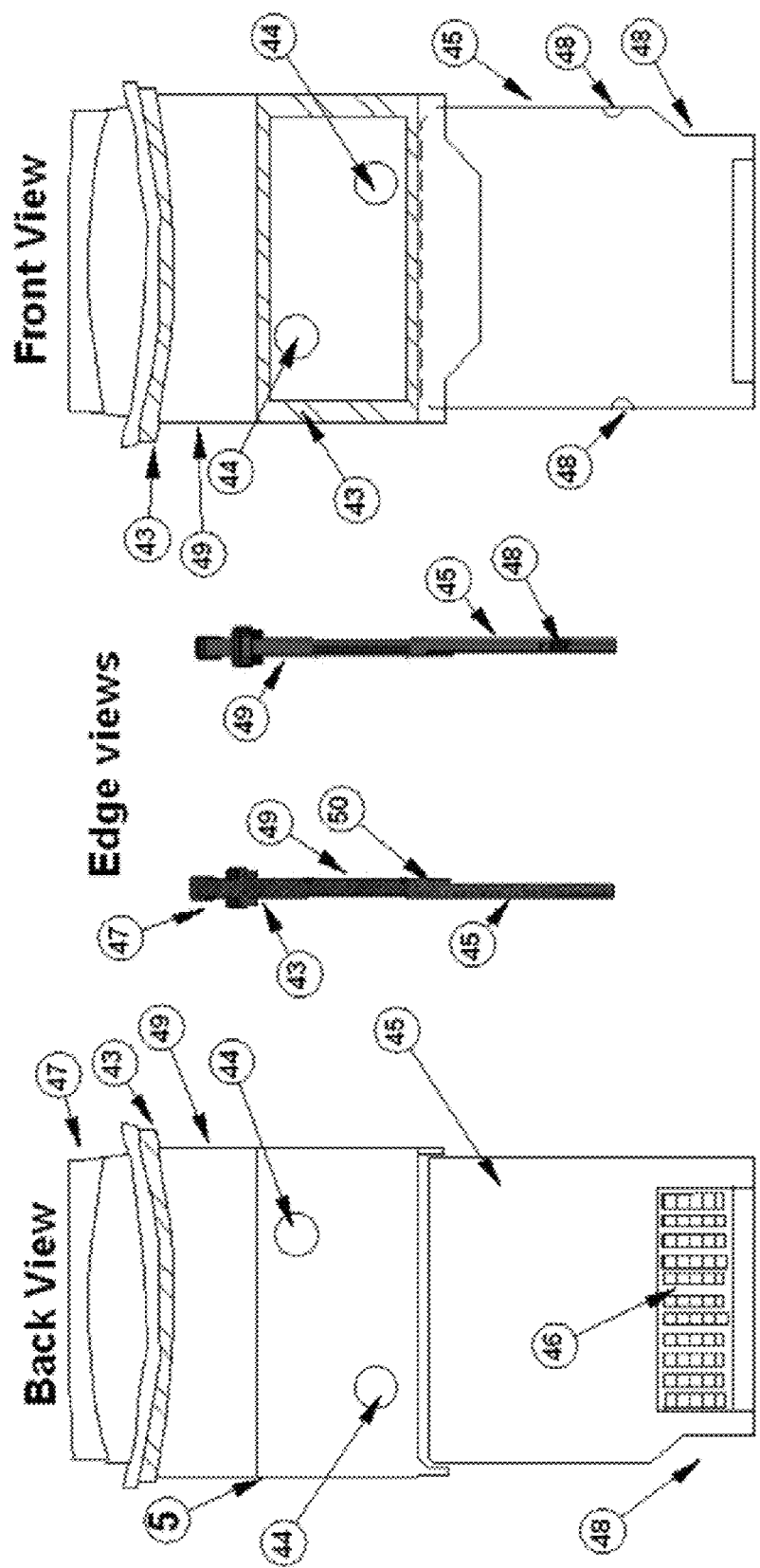
FIG. 5A is a diagram of one embodiment of a disposable sensing cartridge according to the present invention.

FIG. 5A illustrates an embodiment of the disposable sensing cartridge (5) used for glucose breath testing. This cartridge was used to gather the data later provided in different figure as an example of detector output. The cartridge contains two sensor wells (44) one used as a reference and one used to measure the presence and quantify the amount of a specific analyte. The cartridge contains elastomeric seals (43) designed to seal the cartridge top preventing ambient light leaks into the reading device and a second seal surrounds the sensing wells to prevent moisture from entering the reading device. The cartridge design includes a flash memory chip (45) attached to the cartridge bottom using support/alignment lip (50). The cartridge is installed into the reading device via a slot in the top of the case and interfaces with a flash chip socket on the reader Printed Wiring Assembly (PWA) through contact pins (46). Alignment of the cartridge to the light source and photo detectors is accomplished using the alignment features (48) of the Flash Chip. The Flash chip is factory programmed to contain calibration data for the sensors, manufacture date and Lot number, Serial number and expiration date. During use the flash memory also stores data from each test with a date and time stamp and the internal "Self Test", results for the meter each time it is performed. Additional cartridge features include tab (47) which provides a means of holding the cartridge for insertion and removal from the reading device and space (49) for attachment of a manufactures logo.

The cartridge illustrated in FIG. 5B is similar in design to the cartridge illustrated in FIG. 5A. This cartridge (5) contains two sensor/filter assemblies (55, 56) on optically clear substrate (52) supporting a reference channel and a sense channel (44) a lip for attachment of a flash chip (57) an optically transparent seal/cover assembly (51) and flow channels (59) leading to and from analyte well (58). Connection of the cartridge to the liquid flow system is provided via inlet and outlet ports (54 & 53) respectively.

Figure 5C:
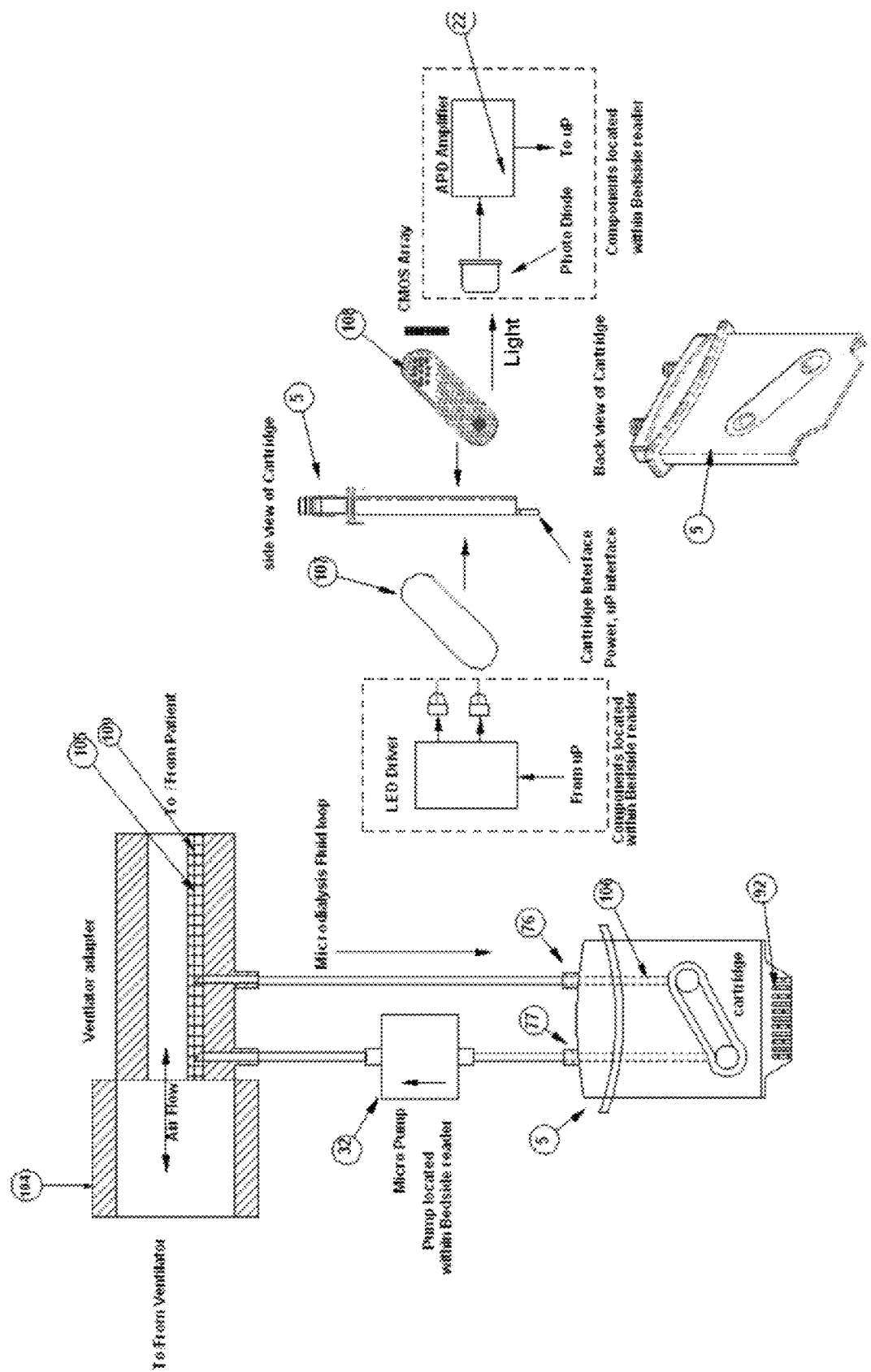
FIG. 5C is a diagram showing one embodiment of a CVASE breath extraction system using a ventilator and liquid flow cartridge according to the present invention.

FIG. 5C illustrates a system using a two channel liquid flow cartridge as in FIG. 5B in a ventilator breath monitoring system, in the event where condensate must be formed in order to detect analytes in condensate. The system is attached in-line with the patient ventilator tubing using adapter (104). Pump (32) is used to extract condensate from a liquid pool formed on TEC (105) cooled extraction plate (109) to sensing cartridge (5) input port (76) leading to cartridge (5) flow channel (106). Once sampled, the condensate can be returned to the ventilator flow path, or it can be directed to a waste contained for proper disposal. Other components of the cartridge and system are similar to those described in FIGS. 5A and 5B. For example, the cartridge (5) contains the cover window (107) and sensor substrate (108) as in FIG. 5B.

Figure 5D:
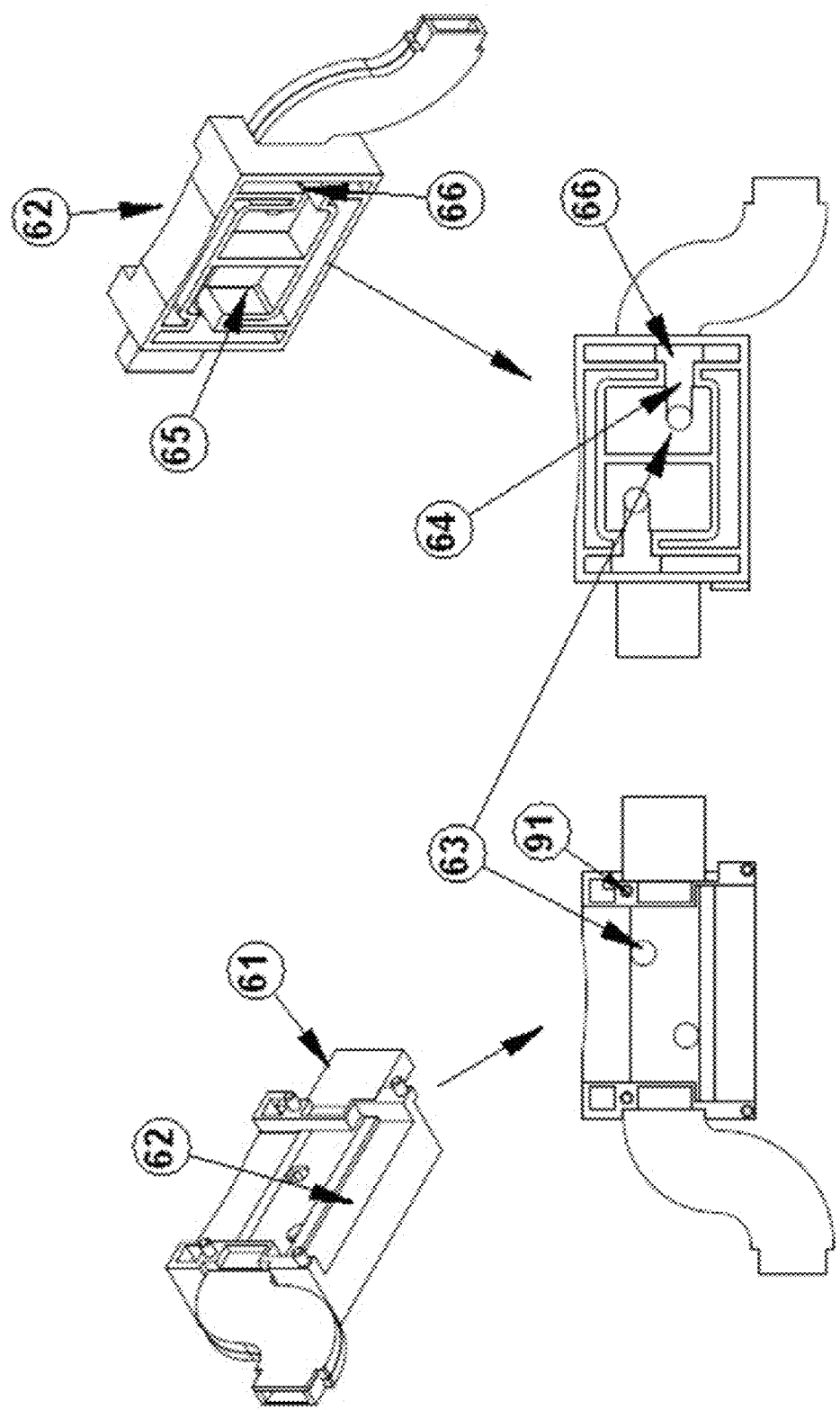
FIG. 5D is a diagram showing one embodiment of a two channel cartridge flow tube PWA mounting holder and assembly according to the present invention.

FIG. 5D illustrates one embodiment of the flow tube assembly that supports the design of the cartridge drawn in FIGS. 5A and 5B. This assembly mounts to the main PWA (Printed Wiring Assembly) of the meter assembly using locating tabs (91) and sits above the photo detectors (also mounted on the main PWA) with the active area of the detectors covered by light coupling holes (63). The sensing cartridge is aligned with the LEDs and photo detectors (PD) by sliding it into slot (62) which guides the cartridge to seat in the flash chip connector on the main PWA. The cartridge is installed with the active sensing area facing toward the breath tube assembly housing. Here a seal is formed between the active face of the cartridge and the breath tube assembly housing bottom by the elastomeric seal (43 in FIG. 5A) of the inserted cartridge. Breath is applied to one end of the tube assembly (61) of the part, using a disposable CVASE apparatus. The top of the assembly contains two rectangular wells (65) that house the light source for each channel. Light intensity control is supported by this assembly through the incorporation of feedback optical fiber guide (64) and feedback photo detector wells (66). The light source and feedback PDs are mounted to a rigid PWA which connects to the main PWA via a flex cable or "Board to Board", connector.

The flow tube assembly illustrated in FIG. 5D supports a two channel cartridge. All cartridge designs include a flash memory chip (45 in FIG. 5A). The two channel cartridge design uses a FLASH chip attached to the cartridge bottom using support/alignment lip (50 in FIG. 5A). The cartridge is installed into the reading device via a slot in the top of the case and interfaces with a flash chip socket on the reader PWA through contact pins (46). The flash chip is factory programmed to contain calibration data for the sensors, manufacture date and lot number, serial number and expiration date. During use the flash memory also stores data from each test with a date and time stamp and the internal "self test", results for the meter each time it is performed. Additional cartridge features include tab (47) which provides a means of holding the cartridge for insertion and removal from the reading device and space (49) for attachment of a manufacturer label or bar code label.

Figure 5E:
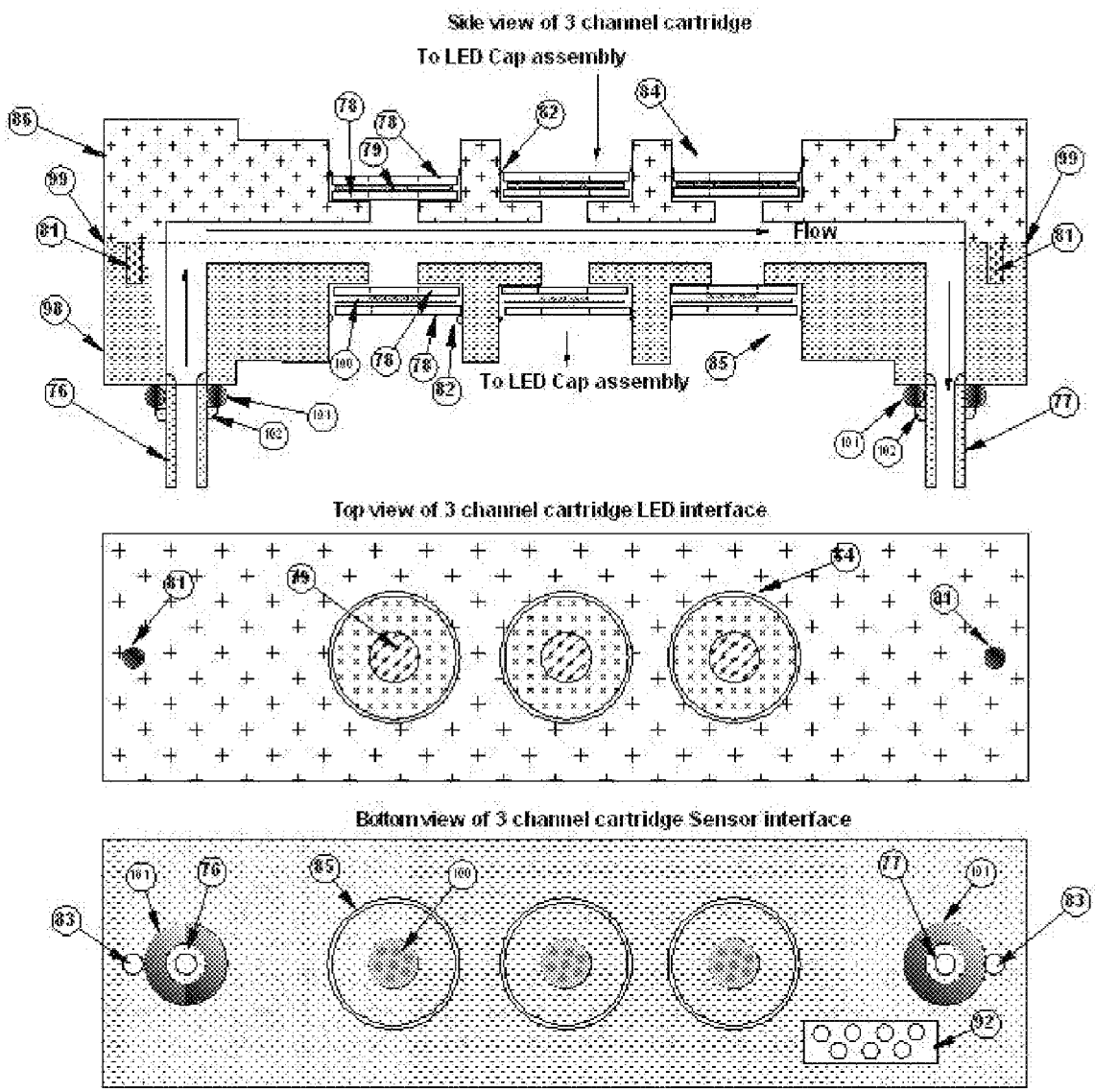
FIG. 5E is a diagram showing one embodiment of a three channel sensing cartridge including a side view with cutaway section according to one embodiment of the present invention.
Figure 5F:
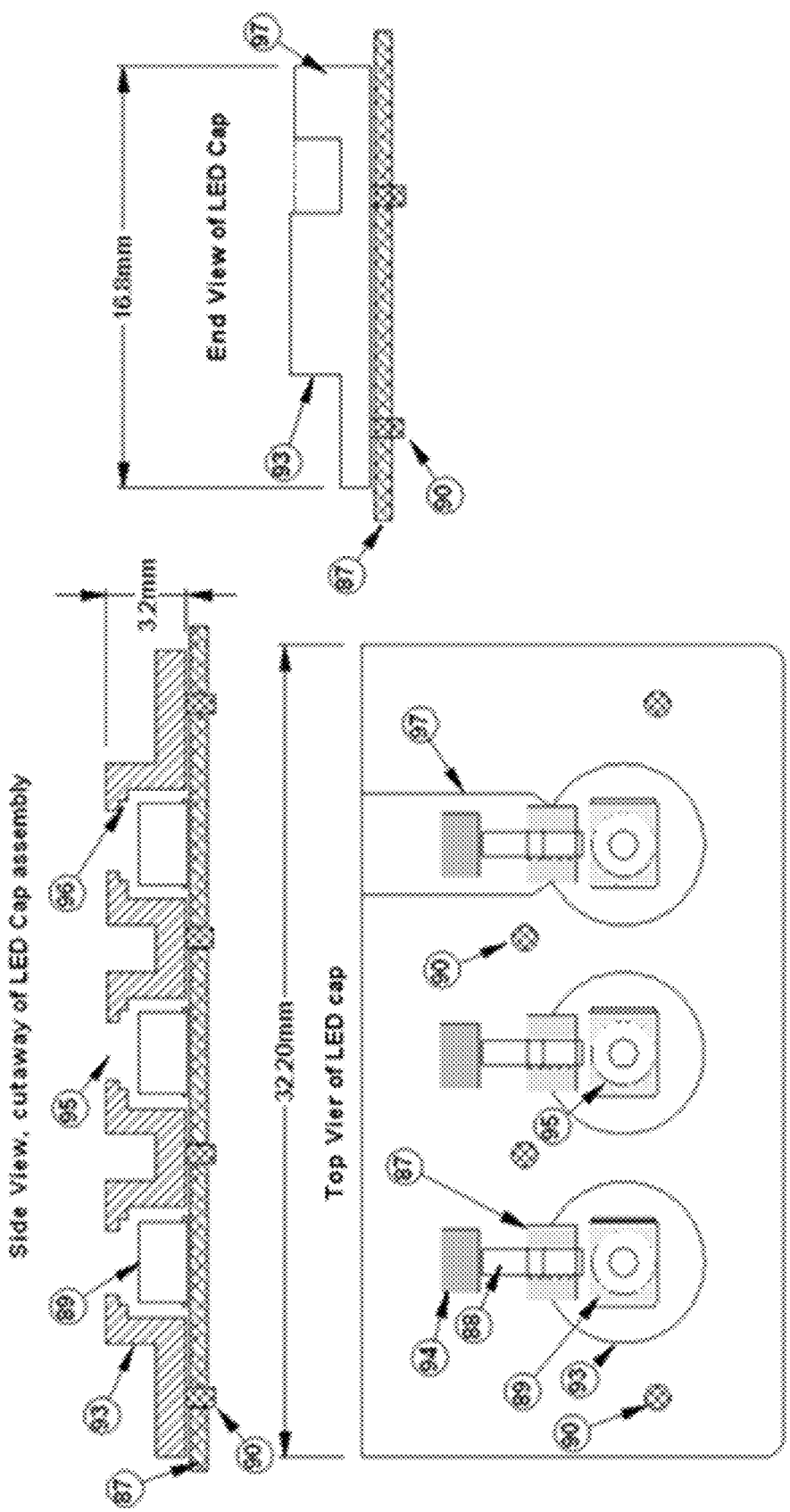
FIG. 5F is a diagram showing a three channel cartridge LED holder and mounting cap assembly according to one embodiment of the present invention.
Figure 5G:
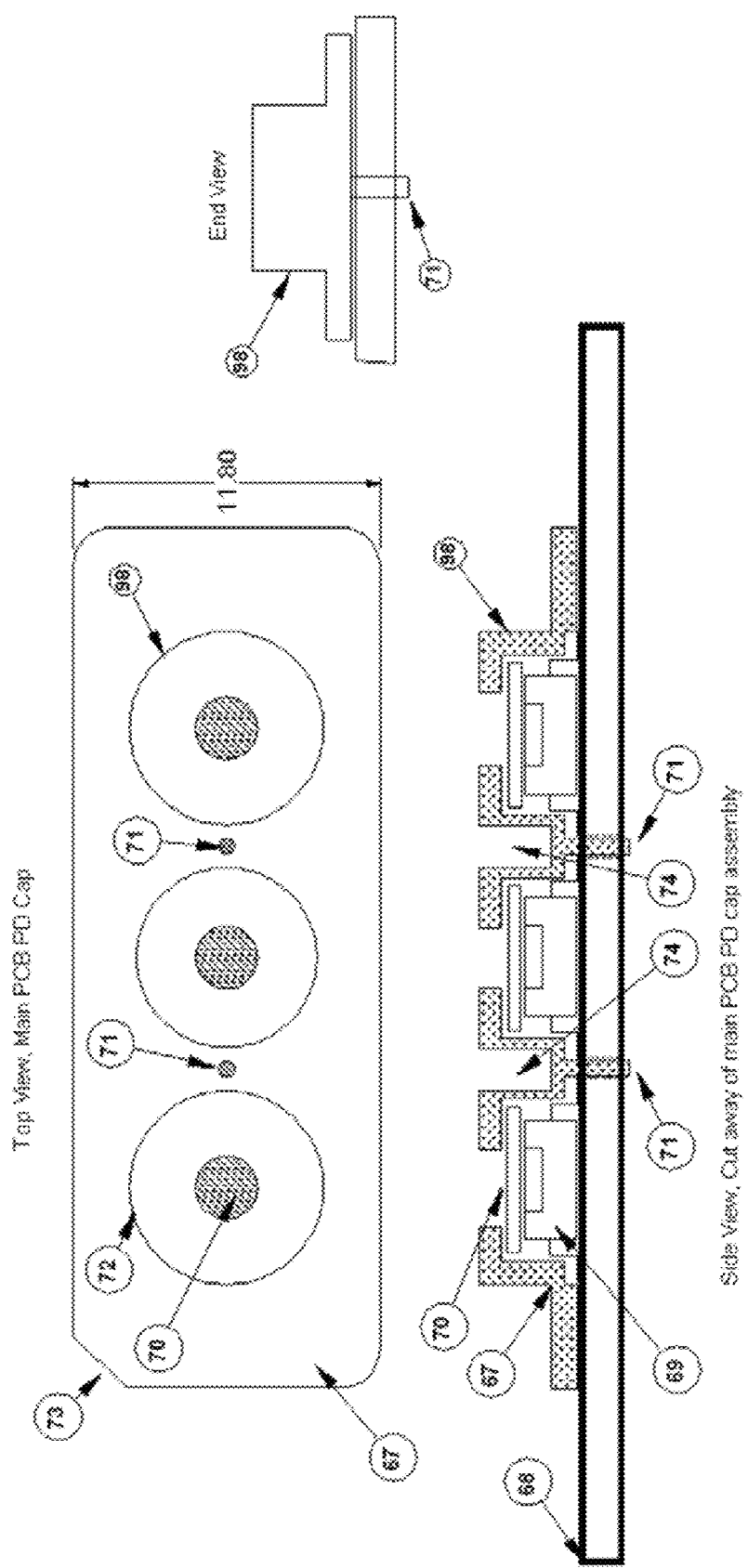
FIG. 5G is a diagram showing a holder cap assembly and attachment to printed wiring assembly (PWA) board according to one embodiment of the present invention.
Figure 5H:
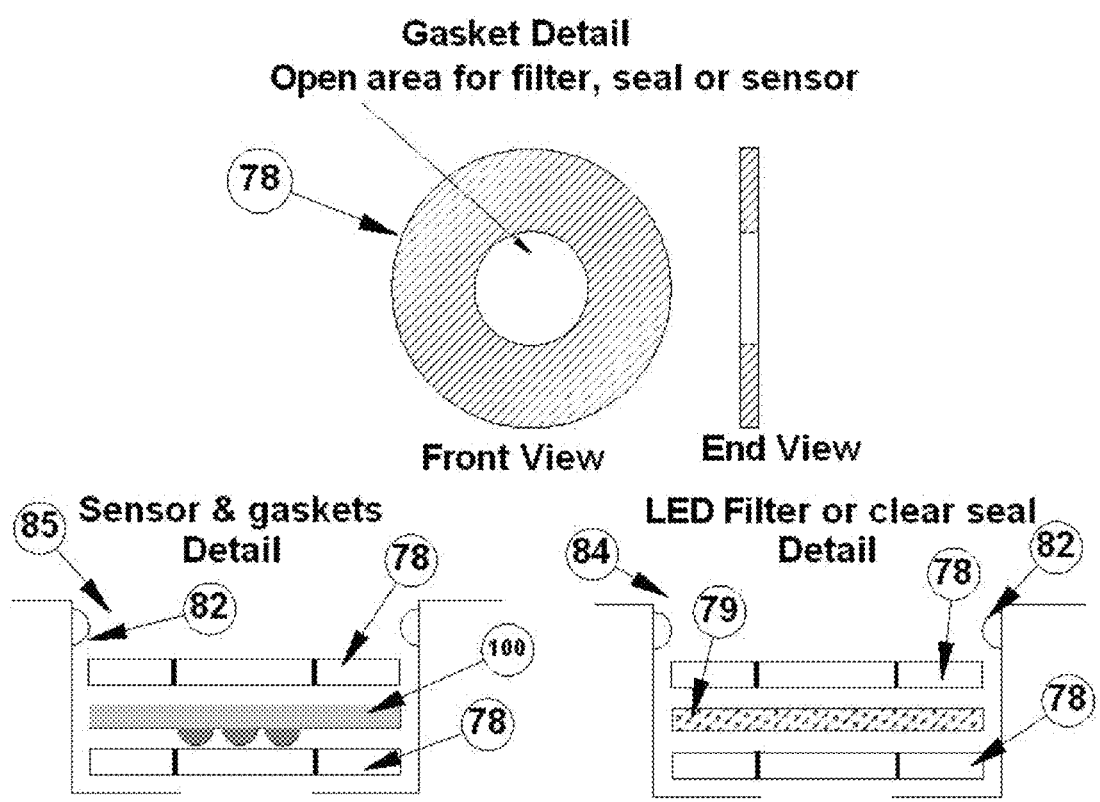
FIG. 5H is a diagram showing a sensing cartridge gasket and sensor placement detail according to one embodiment of the present invention.

Another embodiment of the disposable sensing cartridge assembly is illustrated as FIG. 5E, along with mounting and holding systems as to be detailed as FIG. 5F through FIG. 5H. This example can be used for either liquid or breath media.

FIG. 5E, represents the side (cut-away) view of a three channel sensor cartridge. The cartridge is fabricated in plastic using two mating halves (86) & (98). The top component (86) is designed to mate with a LED cap assembly illustrated in FIG. 4F while the bottom half of the assembly (98) is designed to mate with a photo detector cap assembly illustrated in FIG. 4G. FIG. 5E, mated 3 component sensor cartridge system. This cut away side view of the cartridge illustrates the mechanical interfaces for 3 LEDs on the top (84) and for interface with 3 Photodiodes (85) or other optical detectors on the sensor cartridge bottom of the assembly. The cartridge incorporates a 2 mm fluid path with both inlet and outlet ports (76) and (77) respectively.

The sensor cartridge illustrated as FIG. 5E embodies three sensing channels, an integrated sample (fluid or breath) pathway which has a pump to control presentation of sample. The sensor cartridge has self-alignment features and features designed to prevent improper installation of the cartridge into the reading device. This cartridge design may be used for either fluid or breath and will not leak when used as a disposable sensor cartridge in liquid medium. This cartridge system comprises of three assemblies which are designed for low cost high production volume fabrication and assembly. These assemblies comprise a three channel sensing cartridge housing, a PWA mounted LED cap assembly and a PWA mounted PD cap assembly.

The two pieces of the three channel sensing cartridge (86 & 98) are aligned and held together by pin and socket features (81 & 83). The filters and sensors in each well are sandwiched between two elastomeric gaskets (78), FIG. 5H provides additional detail for the gasket (78), filters (79) and sensor assembly (100). These gaskets are designed to be slightly compressed by the male pegs of the PD and LED caps (see FIGS. 5F, 5G, and 5H) assemblies. The compression on gaskets (78) is sufficient to ensure a leak proof liquid and gas seal between the disposable cartridge and the PD and LED cap components of the meter. The cartridge has an integrated sample flow path which provides an open interface to the sensors (100 in lower left view of cartridge) in each well. The flow path has molded tapered fittings for the inlet (76) and outlet (77) ports and an "O" ring seal (101) designed to provide a leak proof seal through the main PCB using a mating elastomeric sealing system. Mating PWA mounted connectors provide the interface to the fluid source. To facilitate rapid assembly of the cartridge burs (82) are used to provide a stop for the gasket/filter/sensor assemblies prior to assembly of the cartridge halves.

The top of the cartridge interfaces to the LED cap component illustrated in FIG. 5F. This figure represents a cutaway side, top and end views of the three channel sensing cartridge system LED cap components. The LED cap is affixed to a secondary PWA that also contains the light source (89), feedback optical fiber (88) with fiber spacer (87) and feedback PDs (94). These components with the PWA are held in place using compression from the closed lid of the cartridge well in the meter case (not shown).

By exerting downward pressure the LED cap component contributes to a compression seal as does the PD cap assembly from below. The peg diameter differs from the peg diameter for the PD cap which helps prevent incorrect placement of the disposable component.

Two of the sensor cartridge holding components (illustrated in FIGS. 5F and 5G) are rigidly mounted to a PCB and are semi-disposable. These cap assemblies cover the PWA surface mounted LEDs and PDs used in the meter assembly. They are designed to be easily removed and replaced or sterilized after a predetermined use period. The sensing cartridge housing also contains a serial flash memory integrated circuit embedded in the bottom (PD cap side) of the housing. The cartridge is mated with the PD cap assembly memory interface connector (92, FIG. 5F). The connector pins on the main PWA assembly provide an interface between the memory and the meters embedded controller. Alignment of the cartridge to the light source and photo detectors is accomplished using the simple peg and well structure of the cartridge and cap assemblies. Each of these cartridges contains a flash memory chip which interfaces to the main PWA via connector points (92). This memory provides the same features as those described for the two channel cartridge. The flash chip is factory programmed to contain calibration data for the sensors, manufacture date and lot number, serial number and expiration date. During use the flash memory also stores data from each test with a date and time stamp and the internal "Self Test", results for the meter each time it is performed.

Mechanical holding components for the sensor cartridge housing are illustrated FIGS. 5F and 5G. FIG. 5F is the PCB board mounted LED covering component, which is the mounting apparatus on the top holding the 3-channel sensor cartridge in place when inserted as described above. FIG. 5G, is PWA board mounted optical detector covering component, the mounting apparatus on the bottom which holds the 3-channel sensor cartridge housing in place when inserted. The figure shows the side view, top view and end view of the optical detector assembly cap.

FIG. 5G illustrates the PD cap component of this PWA mounted holder for the sensor cartridge. The plastic cap assembly is a semi-disposable and covers the three PDs (69). This assembly is designed to attach to the main PWA (68) of the meter apparatus using alignment/securing pegs (71). The basic form of the cap is a flat plate with three circular pegs (72, 98), when viewed from the side. An optically clear cover seal (70) and or filter are installed inside each peg. The peg location is slightly off center to center and the outside diameter of the pegs is also different. This configuration provides a male interface for the disposable portion of the cartridge and is likely to damage the cartridge if installed improperly.

Figure 6:
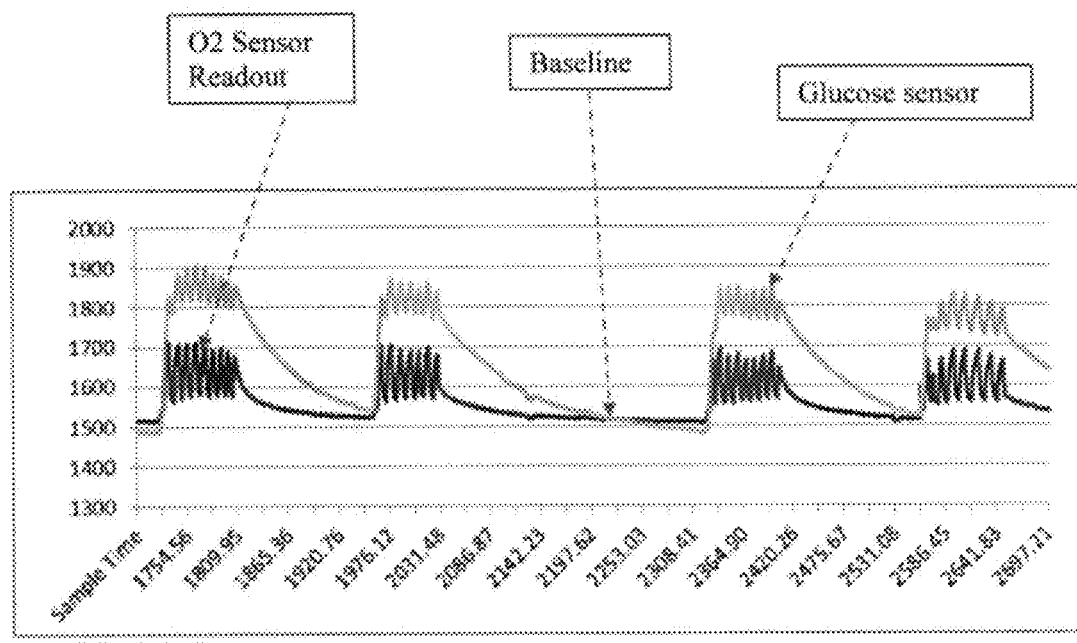
FIG. 6 is a glucose and oxygen sensor response in human breath using one embodiment of a CVASE system according to the present invention.
Figure 7:
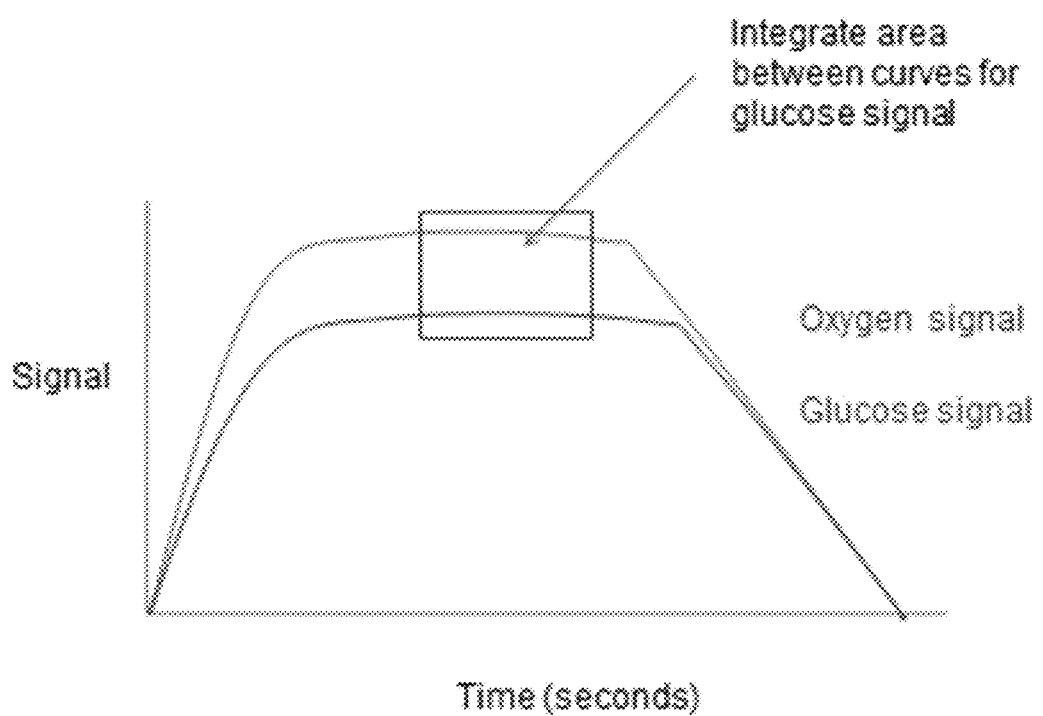
FIG. 7 is a graph illustrating an area under curve (AUC) method of analysis of a glucose and oxygen sensor response according to the present invention.

In FIG. 6, glucose and oxygen sensor response in human breath using CVASE system as in FIG. 4A and providing regulated breath into a two channel cartridge as illustrated in FIG. 5A is shown. FIG. 6 shows an example of a screen capture output from a prototype sensing cartridge for glucose and oxygen measurement in subject breathing at rest using a device of the present invention; including CVASE apparatus to process breath before it enters the sensor device. Multiple breath cycles are shown for each of 6-8 breath pulse groups. The method used for comparative reference based analysis of this data is shown in FIG. 7.

System configurations supporting both breath and liquid flow cartridges have been disclosed. The AUC method can be incorporated into each of these systems to analyze sensor output and quantify analytes in relationship to reference analyte channels. One method of quantification of glucose oxidase sensor response illustrated in FIG. 6 uses the AUC reference method to quantify glucose in breath. Detection limits are 0.1 to 0.3 mmoles.

Figure 8:
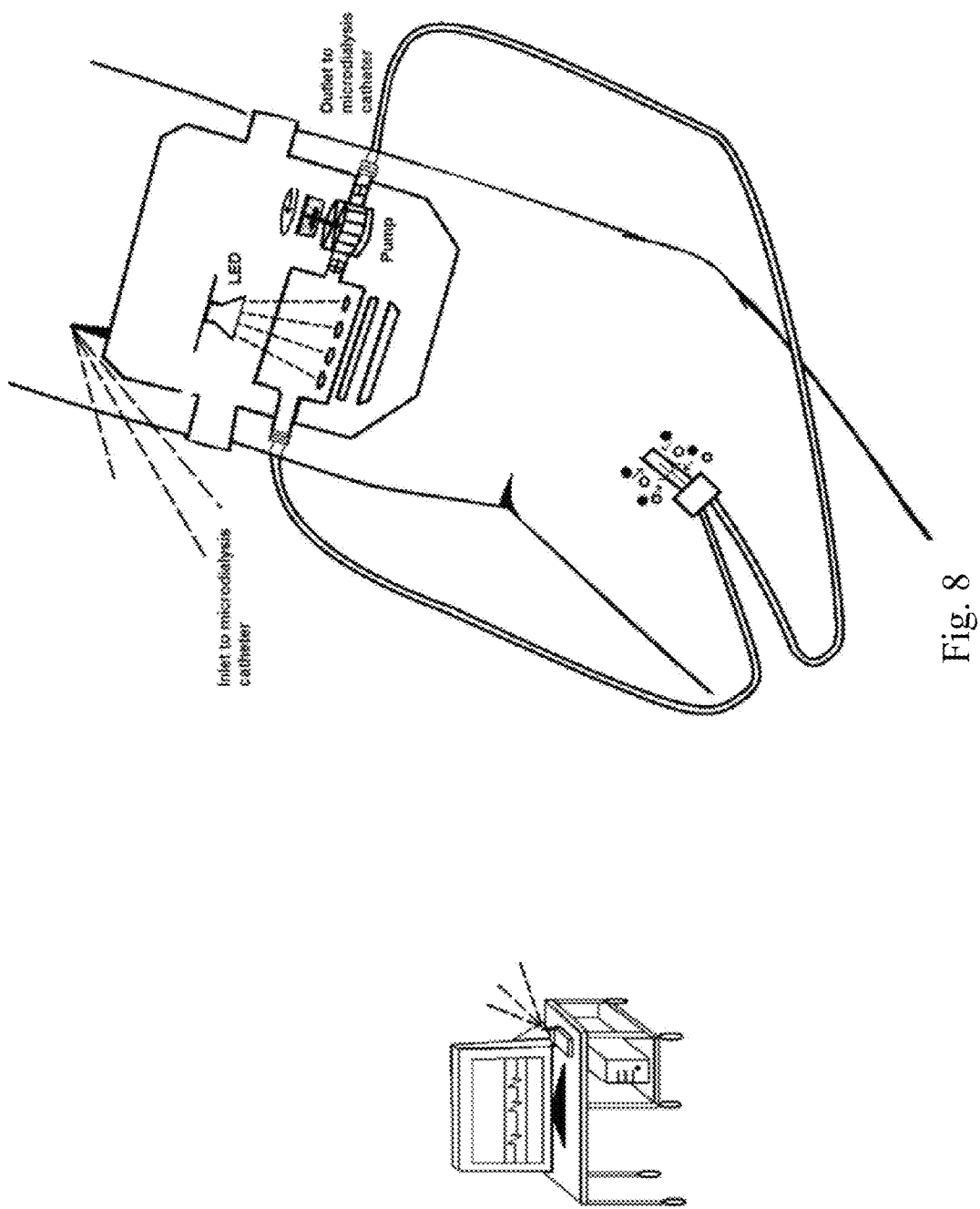
FIG. 8 is a diagram showing a continuous microdialysis system configuration including sensor cartridge, pump and remote data capture, as placed on the arm of a human patient according to one embodiment of the present invention.
Figure 9:
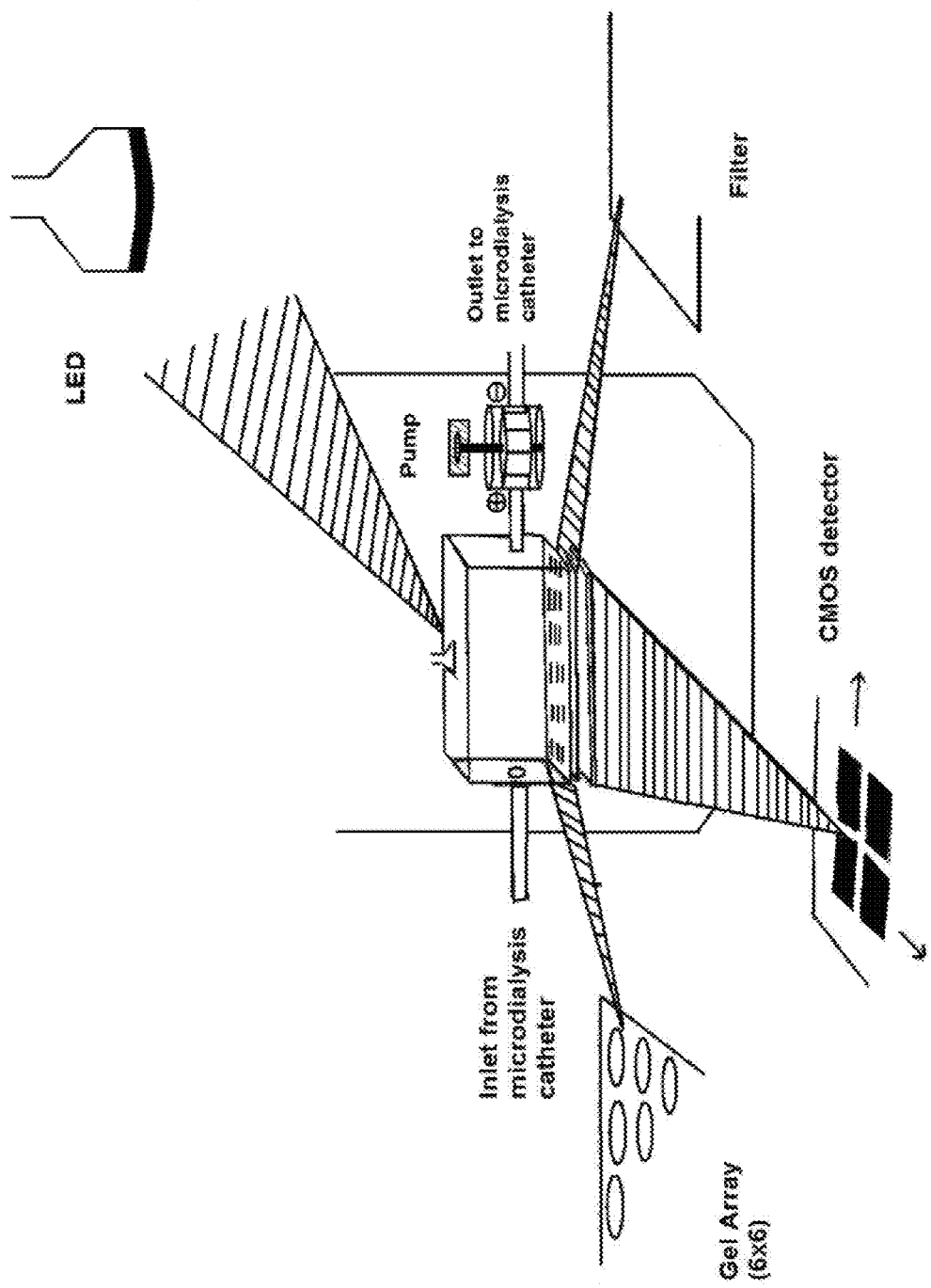
FIG. 9 is a diagram showing a continuous microdialysis system flow detail according to one embodiment of the present invention.

A further embodiment of this invention illustrated in FIG. 8. The diagram in FIG. 8 provides an example for a system which can quantify analytes in micro dialysis fluid extracted by pump and circulated through the sensor cartridge in a closed loop flow system. In this embodiment, microdialysis measurement of larger molecules which equilibrate slowly is enabled. Current single pass microdialysis systems are limited to rapidly equilibrating molecules because of the imbalance between flow rate and equilibration times. The system configuration disclosed here overcomes this limitation and enables the measurement of any molecule that can pass the microdialysis membrane. The illustration provided as FIG. 9 describes the flow and sensor placement for use of the system for analyte measurement in a continuous closed loop micro dialysis fluid.

Figure 10:
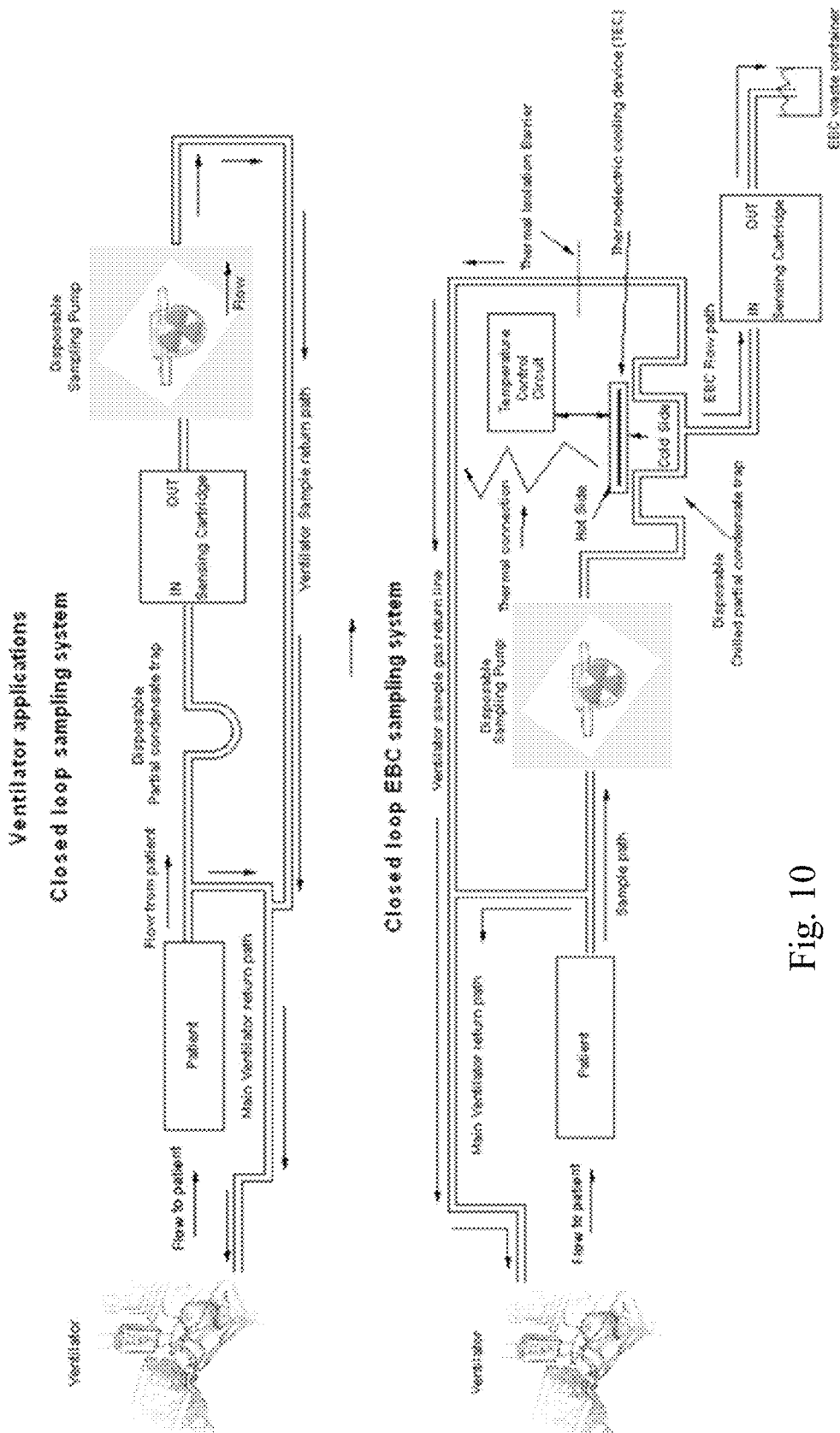
FIG. 10 is a diagram showing examples of continuous breath or exhaled breath condensate (EBC) sampling and analysis as incorporated into the mechanical ventilator of a human patient according to one or more embodiments of the present invention.

FIG. 10 illustrates a use of the sensor cartridge in a ventilator breath measurement system that can detect analyte concentrations in either breath or breath condensate taken from a mechanical ventilator.

In the system illustrated in FIG. 10, placement of the sampling pump in the EBC closed loop example at the bottom of this figure may provide better performance if sampling pump location is positioned at the outlet side of the sensing cartridge rather than the inlet side prior to the EBC collection device as indicated, although either pump placement option does not depart from the use of the system for either continuous sampling of breath or fluids.

One embodiment of the present invention can be described as a continuous volumetric air extraction breath sampling and analyte monitoring system comprising: (a) a volumetric breath collection apparatus pumping the medium containing the analyte thru the sensor cartridge and in regulated contact with the sensor surface; (b) a sensor apparatus where the analyte to be measured is incorporated onto the sensor surface, and the sensor output signal is read by an optical or suitable detector. The detector output values resulting are compared with output values of a reference channel luminescence detector, and using the reference calibrated sensor to report the concentration of an analyte using a sensor and memory storage, the entire system of comparison supporting calibration and measurement scaling of analyte detection and quantification; and (c) a computational means of calibration for sensors used within non-volatile memory of the sensor apparatus.

The sensor apparatus and system can discover and quantify an analyte from a regulated sample of the breath of a human introduced to the apparatus by means of a pump, the sensor apparatus containing at minimum a reference sensor and a sensor for the analyte of interest. The sensor apparatus and system can discover and quantify an analyte from a regulated sample of the body fluid of a human introduced to the sensor by means of a pump. In some cases the reference channel is an oxygen sensor.

The sensor cartridge can include a non-volatile memory used to store factory calibration data for each sensor surface in the cartridge. In some aspects, the non-volatile memory also contains a unique electronic serial number for the sensor. This serial number format will additionally identify date and manufacturing site as well as expiration date for sensor. The non-volatile memory can also be used to record all data gathered during sensor cartridge operation. This data includes, but is not limited to: (a) type of analyte it will detect, by way of example glucose, oxygen, $CO_2$, others; (b) functional data by way of example number of uses, total time in use; and (c) detector outputs from each use including reference channel data.

In some aspects of the present invention the sensor analyte is glucose. Glucose can be measured using xerogel embedded glucose oxidase and the sensor uses luminescence readings to measure oxygen consumption by glucose oxidase enzyme action. The present invention enables oxygen luminescence to be measured and the sensor output of the reference oxygen and the analyte glucose are each computed relative to each other as a measure of fluorescence of the glucose oxidase enzyme action on glucose in breath.

Another embodiment of the present invention can be described as the glucose monitoring method comprising: (a) CVASE quantifying a first analyte concentration measurement in the host or portion thereof using a first single use analyte concentration measurement arrangement; (b) quantifying a second analyte concentration measurement in the host or portion thereof using a second single use analyte concentration measurement arrangement; and (c) making one or more additional analyte concentration measurements during the time period using one or more additional single use analyte concentration measurement arrangement; wherein the analyte concentration measurements of (a) and (b) are automatically made according to a selected schedule contained in the monitoring device to monitor the concentration of the analyte in the host or portion thereof over the given time period.

The glucose sensor of the present invention enables glucose to be measured using a molecular imprint of glucose on the surface of a xerogel, and oxygen is measured simultaneously as a reference analyte. Changes in oxygen luminescence measurement serve as a quantifiable reference for adjustment for human breath cycle variations and disease factors that may alter analyte measurement in breath. The reference measurement could be made using measurable components of breath as alternatives to oxygen, for example $CO_2$, $N_2$, $Cl^-$, $Na^+$, Urea, or a molecular component of blood that readily diffuses from blood to expired air via the lung. Oxygen is a reference and the analyte to be measured relative to the reference may be, by way of example but not limited to sensors specific for $CO_2$, ketones, urea, creatinine, lactic acid, cytokines including TNF, IL-6 and IL-8, CRP, insulin, GLP-1, PYY, GLP-2, bacteria and components thereof, such as endotoxin. In some aspects, oxygen is collected by continuous volumetric air extraction and the measured oxygen is used as a calibration reference to define the concentration of one or more analytes on a second sensor in the same analyte detection pathway as the reference oxygen sensor.

In another embodiment, the air pathway from the continuous volumetric air extraction apparatus obtains air from natural breathing of a mammal, or obtains air from a device engaged in the therapeutic use of oxygen, an example being a mechanical ventilator or oxygen inhalation apparatus. The human breath monitoring system of the present invention can be a device that is hand-held, battery powered, and includes a volumetric means of quantitative air extraction, and includes an optical excitation and optical luminescent measurement system capable of measuring small changes in luminescence of analytes and a reference to calibrate sensors and adjust for differences between breath cycles or patient functional status.

In some embodiments, the optical luminescence detection system comprises a photo-detector, a color filter and a transimpedance amplifier. In one embodiment, the monitoring device accepts disposable luminescence sensors in cartridges, where the cartridges contain, at a minimum, a reference channel for intersubject variations in breath of humans and an analyte detection channel.

In one embodiment, the monitoring device and system of the present invention collects breath using a continuously operating volumetric air sampling and extraction apparatus, called CVASE that collects breath and converts the breath into flowing liquid by use of a condenser apparatus located in proximate airflow to the sensor. In some respects, the analyte is contained in a sample of a body fluid that is presented to the sensor cartridge in a fluid pathway regulated by the pump of the apparatus. The pump controlled flowing liquid may be, by way of example saliva, tears, urine, micro-dialysis fluid, interstitial fluid, bile, cerebrospinal fluid, epithelial lining fluid, wound drainage fluid, and any other suitable body fluid subject to use in measuring analyte concentrations derived from a human.

In another embodiment, the system and device of the present invention utilizes an optical energy source for excitation and that sources can be a LED or LEDs, and the LED drive circuit comprises a programmable current source and an optical feedback path to stabilize LED intensity and color. In one aspect, the LED drive circuit has a range of output values that are factory scaled to fall within a narrow linear portion of the LED forward voltage vs. drive current portion of the curve. This drive range being determined from full output characterization of the LED. The range is further optimized to provide maximum luminescence detection of analytes and reduce bleaching effect of LED output intensity on the sensors to extend sensor life. The present invention can include a USB interface to a computer for transfer of data to a computer for further analysis, or a 802.xx wireless interface to a computer or other wireless device such as a cellular phone for pseudo-real time monitoring of collected data and device performance or for transfer of data to a computer for further analysis. The present device and system may be powered by a user replaced battery, and include a liquid crystal display (LCD) that provides: instructions to a user for operation, displays test results and meter status. The present system and device may also include a simple, intuitive four button interface for device control and use, and/or an audible tone generator and output device for example a speaker. The tones generated being designed to signal proper and improper use of the device as well as system faults detected by the software "Built-In-Test" (BIT), system. In one aspect, the present invention includes a disposable input port and transfer bridge to the sensors supporting breath transfer into and out of the device providing a clean interface for each use. In one embodiment, the present invention uses more than two sensor surfaces in a flowing channel to quantify concentrations of analytes in breath or body fluids of a human patient.

In one embodiment, the present invention includes a multimode smart power control system designed to maximize battery life. The sensor apparatus and monitoring system can use a small rotary or piston pumping device to control the rate of presentation of analytes to the sensor surface in the sensor cartridge. The present system and apparatus can also measure analytes in the breath of humans who breathe at rest into the CVASE apparatus, and analytes in the breath of humans who are receiving mechanical ventilation using the CVASE module to collect breath from the ventilator apparatus. Analytes may be transferred in a pump regulated fashion into the sensor cartridge with volumetric flow of liquid. Analytes may also be collected from breath CVASE and a condenser of breath is directed to produce a volumetric flow of liquid and the liquid is breath condensate.

In some respects, the impeller speed and on/off cycling are provided using a closed loop system with the reference sensor being the main variable input to the controller. In some respects, the present invention uses breath measurements of analytes to monitor diabetes in a home environment of a patient, and/or breath measurements of analytes as sensors to quantify biomarkers of diabetes and diseases of metabolic syndrome and define disease severity, and/or breath measurements of analytes to select treatments and dosages of pharmaceutical treatments for patients with diabetes, obesity, metabolic syndrome or any of the manifestations thereof, and/or uses body fluid measurements of select treatments and dosages of pharmaceutical treatments of patients with diabetes, obesity, metabolic syndrome or any of the manifestations thereof.

The present invention has some embodiments that include an apparatus for use in monitoring the concentration of an analyte in a human over a given period of time, the apparatus comprising: (a) a removable cartridge comprising at least a first and a second single use analyte concentration measurement arrangements; and (b) a device into which the cartridge may be inserted, wherein the device comprises a timing device; and an activation mechanism for automatically activating the measurement means of the cartridge according to a predetermined schedule contained in the device. In some respects the analyte measurement devices make ex vivo measurements. In some aspects, the method measurements are in part triggered according to a timetable programmed by the user or medical personnel.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

We claim:

1. An apparatus for detecting the presence of an analyte in a fluid in a cartridge, the apparatus comprising:
    a tube;
    a first coupling configured to mate with an inlet port of the cartridge;
    a condensate trap in fluid communication between the tube and the first coupling;
    a head assembly having a photodetector interface, the photodetector interface configured to cooperate with a sensor port of the cartridge to expose at least a portion of the photodetector interface to a sensor assembly of the sensor port;
    a tail assembly having an illumination interface, the illumination interface configured to cooperate with an illumination port of the cartridge to provide illumination to a portion of the sensor assembly;
    wherein the head assembly is in clamping relation to the tail assembly such that when a cartridge is disposed between the head and tail assemblies, the head and tail assemblies clamp the cartridge to form a fluidic seal between the illumination interface and illumination port and a fluidic seal between the photodetector interface, sensor assembly, and sensor port.

2. The apparatus of claim 1, further comprising a pump configured to move fluid through a cartridge disposed between the head and tail assemblies.

3. The apparatus of claim 1, further comprising a processor in electronic communication with the photodetector interface, the processor configured to capture analyte detection information from the photodetector interface.

4. The apparatus of claim 2, further comprising a flow sensor, the processor configured to regulate the flow of fluid through the cartridge based on output from the flow sensor.

5. The apparatus of claim 1, wherein the head and tail assemblies clamp the cartridge to also form a lightproof seal.

6. The apparatus of claim 1, wherein the sensor assembly is only exposed to light from the illumination interface.

7. The apparatus of claim 1, wherein the apparatus further comprises multiple photo detector interfaces and sensor ports.

8. The apparatus of claim 1, wherein the apparatus further comprises multiple illumination interfaces and illumination ports.

9. An apparatus for detecting the presence of an analyte in a fluid in a cartridge, the apparatus comprising:
- a tube;
- a first coupling configured to mate with an inlet port of the cartridge;
- a condensate trap in fluid communication between the tube and the first coupling;
- a head assembly and a tail assembly, either the head assembly or the tail assembly having a photo detector interface, the photo detector interface configured to cooperate with a sensor port of the cartridge to expose at least a portion of the photo detector interface to a sensor assembly of the sensor port;
- wherein the head assembly is in clamping relation to the tail assembly such that when a cartridge is disposed between the head and tail assemblies, the head and tail assemblies clamp the cartridge to form a fluidic seal between the photo detector interface, sensor assembly, and sensor port.

10. The apparatus of claim 1, further comprising a second coupling configured to mate with an outlet port of the cartridge.

11. The apparatus of claim 1, wherein the condensate trap includes a thermoelectric device.

* * * * *